US012599647B2

(12) United States Patent
Mo et al.

(10) Patent No.: US 12,599,647 B2
(45) Date of Patent: Apr. 14, 2026

(54) PEPTIDE AMIDE COMPOSITION AND PREPARATION METHOD THEREFOR

(71) Applicant: Xizang Haisco Pharmaceutical Co., Ltd., Tibet (CN)

(72) Inventors: Yi Mo, Chengdu (CN); Honghu Li, Chengdu (CN); Li Zhang, Chengdu (CN); Xiangling Ma, Chengdu (CN); Can Zhao, Chengdu (CN)

(73) Assignee: Xizang Haisco Pharmaceutical Co., Ltd., Tibet (CN)

( * ) Notice: Subject to any disclaimer, the term of this patent is extended or adjusted under 35 U.S.C. 154(b) by 1021 days.

(21) Appl. No.: 17/637,189

(22) PCT Filed: Aug. 24, 2020

(86) PCT No.: PCT/CN2020/110760
§ 371 (c)(1),
(2) Date: Feb. 22, 2022

(87) PCT Pub. No.: WO2021/036975
PCT Pub. Date: Mar. 4, 2021

(65) Prior Publication Data

US 2022/0305074 A1 Sep. 29, 2022

(30) Foreign Application Priority Data

Aug. 23, 2019 (CN) ......................... 201910751700.7

(51) Int. Cl.

| | |
|---|---|
| ***A61K 47/00*** | (2006.01) |
| ***A61K 9/00*** | (2006.01) |
| ***A61K 9/19*** | (2006.01) |
| ***A61K 38/07*** | (2006.01) |
| ***A61K 47/12*** | (2006.01) |
| ***A61K 47/18*** | (2017.01) |
| ***A61K 47/26*** | (2006.01) |

(52) U.S. Cl.
CPC ............ *A61K 38/07* (2013.01); *A61K 9/0019* (2013.01); *A61K 9/19* (2013.01); *A61K 47/12* (2013.01); *A61K 47/183* (2013.01); *A61K 47/26* (2013.01)

(58) Field of Classification Search
CPC ........ A61K 38/07; A61K 47/02; A61K 47/12; A61K 9/0019; A61K 9/19; A61K 47/183; A61K 38/00; C07K 5/10; C07K 5/1016
See application file for complete search history.

(56) References Cited

U.S. PATENT DOCUMENTS 5,739,118 A * 4/1998 Carrano ............... A61K 39/292 514/35
7,402,564 B1 7/2008 Schteingart et al.
8,299,209 B2 * 10/2012 Lambert ................ A61K 38/31 530/317
11,014,964 B2 * 5/2021 Zhang .................. C07K 5/1024
2009/0075907 A1 3/2009 Schteingart et al.
2009/0325978 A1 * 12/2009 Onai ........................ A61K 9/19 514/254.1
2015/0031630 A1 * 1/2015 Nestor .................... A61P 19/00 536/4.1
2016/0206649 A1 * 7/2016 Story ...................... A61L 27/50
2017/0158763 A1 * 6/2017 Gauthier .................. A61K 9/08
2018/0125786 A1 * 5/2018 Cho ..................... A61K 9/0019
2020/0172573 A1 * 6/2020 Zhang .................. C07K 5/1016
2021/0040150 A1 * 2/2021 Liao ......................... C07K 7/02
2021/0100886 A1 * 4/2021 Ban .................... C07K 14/4748
2022/0305074 A1 9/2022 Mo et al.

FOREIGN PATENT DOCUMENTS

AU 2020338767 A1 3/2022
CN 1666741 A 9/2005
CN 1895251 A 1/2007
CN 101627049 A 1/2010
(Continued)

OTHER PUBLICATIONS

Extended European Search Report for EP Application No. 20855974.0, mailed Nov. 10, 2022, 9 pages.
Office Action for Eurasian Application No. 202290547/25, mailed Aug. 4, 2022, 2 pages.
Office Action for Indian Application No. 202217015840, mailed Aug. 29, 2022, 6 pages.
Wang et al., Review of Excipients and pH's for Parenteral Products Used in the United States, PDA Journal of Pharmaceutical Science and Technology, vol. 34, No. 6, 452-462, Nov. 1980, 6 pages.
(Continued)

*Primary Examiner* — Jeanette M Lieb
(74) *Attorney, Agent, or Firm* — Foley & Lardner LLP

(57) ABSTRACT

Disclosed are a peptide amide compound composition, a preparation method therefor and medical use thereof. Specifically, the composition contains a compound of formula (I) and pH regulators, and the pH of the solution thereof is 3-5.5. The composition is stable and requires few excipients, and is stable in clinical use. The composition is used for treating or preventing a disease or condition associated with kappa opioid receptors (I)

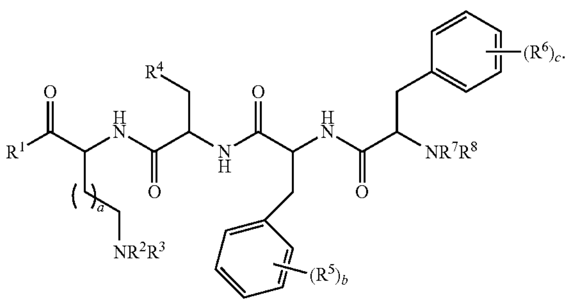

19 Claims, 1 Drawing Sheet

(56) References Cited

FOREIGN PATENT DOCUMENTS

| | | | |
|---|---|---|---|
| CN | 109280075 | A | 1/2019 |
| CN | 109280076 | A | 1/2019 |
| EP | 3 656 782 | A1 | 5/2020 |
| EP | 4 019 033 | A1 | 6/2022 |
| WO | WO-2008/057608 | A2 | 5/2008 |
| WO | WO-2019/015644 | A1 | 1/2019 |
| WO | WO-2021/036975 | A1 | 3/2021 |

OTHER PUBLICATIONS

First Office Action for Indonesian Application No. P00202203493, issued Nov. 21, 2023, 6 pages.
Second Office Action for Chinese Application No. 202080058211.4, dated Nov. 17, 2023, 10 pages.
Wang et al., Fundamentals of Medical Chemistry, Textbooks for higher medical colleges and universities, 2004, 5 pages.
First Office Action and Search Report for CN Application No. 202080058211.4, dated May 31, 2023, 12 pages.
Office Action for JP Application No. 2022-511294, mailed Jul. 18, 2023, 6 pages.
Office Action from CA Application No. 3,152,065, dated Aug. 7, 2023, 3 pages.
Office Action for JP Application No. 2022-511294, mailed Jan. 26, 2024, 5 pages.
English and Chinese language versions of International Search Report and Written Opinion for International Application No. PCT/CN2020/110760, mailed Dec. 1, 2020, 15 pages.
Belgaid et al., Sterilization of aseptic drug by sterile filtration: Microbiology validation by microbiology challenge test, Journal of Chemical and Pharmaceutical Research, vol. 6, No. 12, 760-770, 2014, 11 pages.
Office Action for Eurasian Application No. 202290547/28, mailed Jan. 18, 2023, 6 pages.
Pramanick et al., Excipient Selection In Parenteral Formulation Development, Pharma Times, vol. 45, No. 3, 65-77, Mar. 2013, 13 pages.
Examination Report No. 1 for Australian Patent Application No. 2020338767, dated Jun. 4, 2024, 4 pages.
Office Action for Japanese Application No. 2022-511294, mailed Jun. 4, 2024, 4 pages.
Office Action for Malaysian Application No. PI2022000959, dated Jul. 29, 2024, 5 pages.
Second Office Action for Indonesian Application No. P00202203493, issued Aug. 23, 2024, 6 pages.
Office Action for KR Application No. 10-2022-7009340, dated Jan. 16, 2025, 9 pages.
Office Action for MX Application No. MX/a/2022/002187, dated Jan. 27, 2025, 9 pages.

* cited by examiner

PEPTIDE AMIDE COMPOSITION AND PREPARATION METHOD THEREFOR

CROSS-REFERENCE TO RELATED APPLICATIONS

This application is a National Stage of International Application No. PCT/CN2020/110760, filed on Aug. 24, 2020, which claims priority to Chinese Patent Application No. 201910751700.7, filed on Aug. 23, 2019, both of which are hereby incorporated by reference herein in their entireties.

TECHNICAL FIELD

The present disclosure belongs to the field of medicine and relates to a peptide amide compound composition having analgesic effects, a preparation method therefor and medical use thereof.

BACKGROUND ART

Opioid drugs have been used to treat pains for thousands of years and play a physiological role primarily by binding to three known classic opioid receptors, i.e., mu, delta and kappa opioid receptors. These three receptors are all members of the G protein-coupled receptor family, are mainly distributed in the central nervous system, and also exist in many peripheral tissues. One of the most classic drugs is morphine, which exerts an analgesic effect mainly through the action of p opioid receptors.

CN 101627049 discloses a class of synthetic peptide amide ligands of kappa opioid receptors, which have the effects of treating pains, inflammation, itching, edema, hyponatremia, hypokalemia, intestinal obstruction, cough and glaucoma and comprise a compound having the structure below and a development code of CR845:

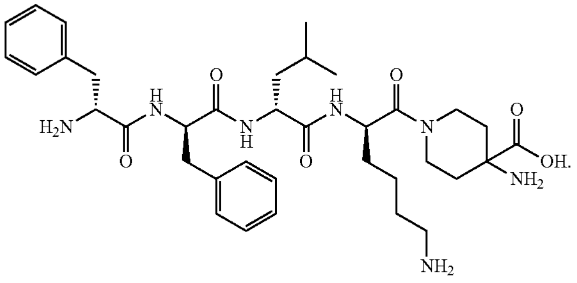 [SMILES: CC(C)C[C@@H](NC(=O)[C@@H](Cc1ccccc1)NC(=O)[C@H](N)Cc1ccccc1)C(=O)N[C@H](CCCCN)C(=O)N1CCC(N)(C(=O)O)CC1]

WO 2019015644 A1 discloses a class of peptide amide compounds having analgesic effects, kappa opioid receptors, and a compound comprising the structure below, which is referred to as compound II:

(II)

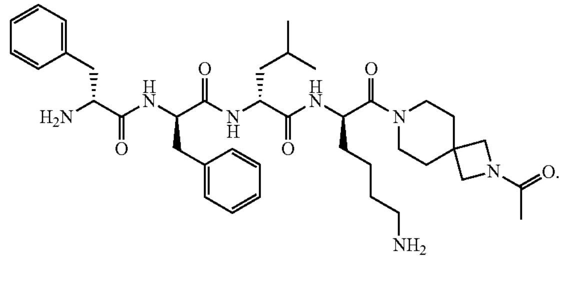

Preclinical studies of the compound show that the compound has potent and long-acting effects on analgesia and itching treatment, and while exerting peripheral analgesic and anti-pruritic efficacies, the compound can reduce side effects associated with opioid drugs on the central nervous system.

There are currently no kappa opioid receptor peptide amide compounds on the market and no disclosure of compositions and related preparations thereof.

SUMMARY OF THE INVENTION

The present disclosure aims to provide a pharmaceutical composition with stability, high efficacy, low dosage, reliable safety, good compliance and low cost.

The composition of the present disclosure can be a small-volume solution for injection, or a sterile lyophilized powder for injection.

The composition of the present disclosure can realize large-scale production, and the obtained product is stable and excellent in safety and can be used as medicines for the treatment of acute and chronic pain, pruritus, etc.

The present disclosure relates to a pharmaceutical composition comprising a compound of formula (I) below or a pharmaceutically acceptable salt thereof and a pH regulator, wherein the composition has a pH value of 3-5.5, (I)

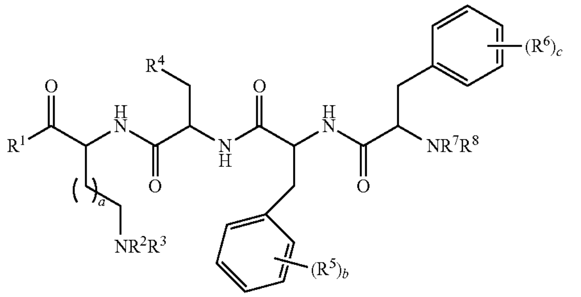

wherein $R^1$ is selected from

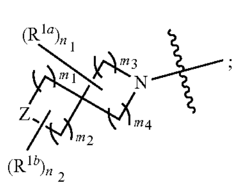

$m_1$ and $m_2$ are each independently selected from 1, 2, 3 or 4;

$m_3$ and $m_4$ are each independently selected from 0, 1, 2, 3 or 4, provided that $m_3$ and $m_4$ are not both 0;

$n_1$ and $n_2$ are each independently selected from 0, 1, 2, 3 or 4;

Z is selected from $CR^{z1}R^{z2}$ or $NR^{z3}$;

$R^{z1}$ and $R^{z2}$ are each independently selected from H, F, Cl, Br, I, OH, $CF_3$, nitro, $C_{1-6}$alkyl, $C_{1-6}$alkoxy, $C_{2-6}$alkenyl, $C_{2-6}$alkynyl, $-C(=O)-C_{1-6}$alkyl, $-(CH_2)_q-C(=O)O-C_{1-6}$alkyl, $-(CH_2)_q-NR^{1e}R^{1f}$, $-(CH_2)_q-COOH$, $-(CH_2)_q-CONH_2$, $C_{3-8}$carbocyclyl, or 3- to 8-membered heterocyclyl, wherein the alkyl, alkoxy, alkenyl, alkynyl, carbocyclyl or heterocyclyl is optionally further substituted with 0-5 substituents selected from F, Cl, Br, I, OH, $CF_3$, =O, carboxyl, nitro, cyano, amino, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, the heterocyclyl contains 1 to 3 heteroatoms optionally selected from N, O or S, and when the heteroatom is S, the heterocyclyl can optionally contain S, S=O or S(=O)$_2$;

$R^{1e}$ and $R^{1f}$ are each independently selected from H, $C_{1-6}$alkyl, —C(=O)O—$C_{1-6}$alkyl, —C(=O)O—$(CH_2)_q$—$C_{3-8}$carbocyclyl, or —C(=O)O—$(CH_2)_q$—3- to 8-membered heterocyclyl, wherein the alkyl, carbocyclyl or heterocyclyl is optionally further substituted with 0-5 substituents selected from F, Cl, Br, I, OH, $CF_3$, cyano, nitro, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, and the heterocyclyl contains 1 to 3 heteroatoms selected from N, O or S;

or $R^{z1}$ and $R^{z2}$ together with the carbon atoms to which they are attached form a 3- to 10-membered nitrogen-containing heterocyclic ring, wherein the ring is optionally further substituted with a substituent selected from F, Cl, Br, I, OH, $CF_3$, cyano, nitro, =O, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl;

$R^{1a}$ and $R^{1b}$ are each independently selected from F, $CF_3$, $C_{1-6}$alkyl, $C_{2-6}$alkenyl, $C_{2-6}$alkynyl or 3- to 8-membered heterocyclyl, wherein the alkyl, alkenyl, alkynyl or heterocyclyl is optionally further substituted with 0-5 substituents selected from F, Cl, Br, I, OH, $CF_3$, nitro, cyano, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, and the heterocyclyl contains 1 to 3 heteroatoms optionally selected from N, O or S;

$R^{z3}$ is independently selected from H, —C(=O)—$C_{1-6}$alkyl, —C(=O)O—$C_{1-6}$alkyl, —C(=O)—$C_{3-8}$carbocyclyl, —C(=O)O—$C_{3-8}$carbocyclyl, —C(=O)O-(3- to 8-membered heterocyclyl), —S(=O)$_p$—$C_{1-6}$alkyl, —S(=O)$_p$—$C_{3-8}$carbocyclyl, —S(=O)$_p$-(3- to 8-membered heterocyclyl), —C(=O)NR$^{1g}$R$^{1h}$, —S(=O)$_p$—NR$^{1i}$R$^{1j}$ or 3- to 8-membered heterocyclyl, wherein the alkyl, carbocyclyl or heterocyclyl is optionally further substituted with 0-5 substituents selected from F, Cl, Br, I, OH, $CF_3$, nitro, cyano, amino, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, and the heterocyclyl contains 1 to 3 heteroatoms optionally selected from N, O or S;

$R^{1g}$, $R^{1h}$, $R^{1i}$, and $R^{1j}$ are each independently selected from H or $C_{1-6}$alkyl;

or $R^{1g}$ and $R^{1h}$ together with the nitrogen atoms to which they are attached form a 3- to 10-membered heterocyclic ring, wherein the ring is optionally further substituted with a substituent selected from F, Cl, Br, I, OH, $CF_3$, cyano, nitro, $C_{1-6}$alkyl, $C_{1-6}$alkoxy, $C_{2-6}$alkenyl, $C_{2-6}$alkynyl or —S(=O)$_p$—$C_{1-6}$alkyl, and the heterocyclic ring contains 1 to 3 heteroatoms selected from N, O or S;

q is selected from 0, 1, 2, 3 or 4;

p is selected from 0, 1 or 2;

a is selected from 0, 1, 2 or 3;

$R^4$ is independently selected from H, $C_{1-6}$alkyl, $C_{2-6}$alkenyl, $C_{2-6}$alkynyl or —$(CH_2)_q$—$C_{3-8}$carbocyclyl, wherein the alkyl, alkenyl, alkynyl or carbocyclyl is optionally further substituted with 0-5 substituents selected from F, Cl, Br, I, OH, CN, $CF_3$, $NO_2$, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, and the heterocyclyl contains 1 to 3 heteroatoms selected from N, O or S;

$R^2$, $R^3$, $R^7$ and $R^8$ are each independently selected from H, $C_{1-6}$alkyl, —C(=O)O—$C_{1-4}$alkyl, —C(=O)O—$(CH_2)_q$—$C_{3-8}$carbocyclyl, —C(=O)O—$(CH_2)_q$-3- to 8-membered heterocyclyl or

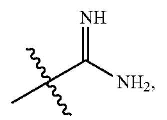 [SMILES: *C(=N)N]

wherein the alkyl, carbocyclyl or heterocyclyl is optionally further substituted with 0-5 substituents selected from F, Cl, Br, I, OH, $CF_3$, nitro, cyano, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, and the heterocyclyl contains 1 to 3 heteroatoms optionally selected from N, O or S;

b is selected from 0, 1, 2, 3, 4 or 5;

c is selected from 0, 1, 2, 3, 4 or 5;

$R^5$ and $R^6$ are each independently selected from F, Cl, Br, I, $CF_3$, cyano, nitro, $C_{1-4}$alkyl, —OR$^{5a}$, —C(O)OR$^{5b}$, —SR$^{5c}$, —S(O)R$^{5d}$, +S(O)$_2$R$^{5e}$ or —NR$^{5f}$R$^{5g}$;

$R^{5a}$, $R^{5b}$, $R^{5c}$, $R^{5d}$, $R^{5e}$, $R^{5f}$ and $R^{5g}$ are each independently selected from H or $C_{1-4}$alkyl;

or $R^{5f}$ and $R^{5g}$ together with the nitrogen atoms to which they are attached form a 5- to 6-membered heterocyclic ring, wherein the heterocyclic ring contains 1 to 3 heteroatoms optionally selected from N, O or S.

The composition has a pH of 3-5.5, and the composition is stable. In certain embodiments, the pH value of the composition is 3-5; in certain embodiments, the pH value is 3-4.5; in certain embodiments, the pH value is 3.5-4.5; in certain embodiments, the pH value is 4-4.5, and in certain embodiments, the pH value is 3.5-4.3.

The compound of formula (I) in the present disclosure has a structure of formula (II):

(II)

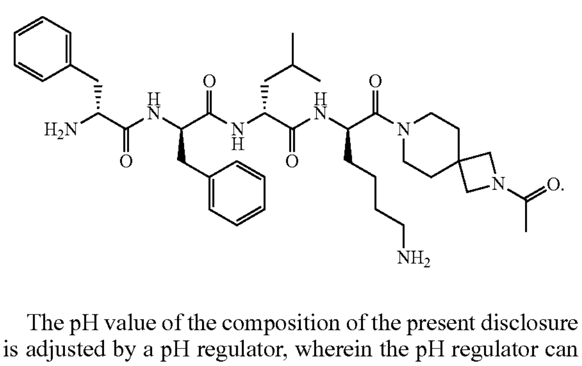

The pH value of the composition of the present disclosure is adjusted by a pH regulator, wherein the pH regulator can be any pharmaceutically acceptable inorganic acid or organic acid, wherein the inorganic acid includes sulfuric acid, hydrochloric acid, phosphoric acid, etc., and the organic acid includes acetic acid, benzoic acid, tartaric acid, lactic acid, methanesulfonic acid, citric acid, maleic acid, etc. The pH regulator can also be a buffer consisting of acids and salts and having a pH value in the range of 3-5.5, and the buffer is a buffer system consisting of an acid and a corresponding salt thereof, such as an acetic acid-acetate buffer system, a tartaric acid-tartrate buffer system, and a benzoic acid-benzoate buffer system.

The pH regulator of the composition of the present disclosure is selected from a buffer, which is selected from an acetic acid-acetate buffer, a phosphoric acid-phosphate buffer, a tartaric acid-tartrate buffer or a benzoic acid-benzoate buffer; in certain embodiments, the buffer is selected from an acetic acid-sodium acetate buffer, a phosphoric acid-phosphate (a sodium salt) buffer, and a tartaric acid-tartrate (a sodium salt) buffer; and in certain embodiments, the buffer is selected from an acetic acid-sodium acetate buffer.

The pH regulator of the present disclosure is selected from a buffer. The concentration of the buffer can be 1 mmol/L-500 mmol/L; in certain embodiments, the concentration is 2 mmol/L-100 mmol/L; in certain embodiments, the concentration is 2 mmol/L-80 mmol/L; in certain embodiments, the concentration is 5 mmol/L-80 mmol/L; and in certain embodiments, the concentration is 10 mmol/L-50 mmol/L.

It should be noted that the concentration of the pH regulator is the sum of the concentration of a weak acid and all corresponding salts thereof. With regard to a weak monoacid buffer system, such as an acetic acid-sodium acetate buffer, the concentration of the pH regulator is the sum of the concentration of HAc (acetic acid) and $Ac^-$ (an acetate ion); and with regard to a weak polyacid buffer system, such as a phosphoric acid-phosphate buffer, the concentration of the pH regulator is the sum of the concentration of $H_3PO_4$, $H_2PO_4^-$, $HPO_4^{2-}$ and $PO_4^{3-}$ present in a solution.

In the composition of the present disclosure, the weight/volume ratio, w/v, of the compound of formula (I) is 0.001%-5%; in certain embodiments, the w/v is 0.001%-2%; in certain embodiments, the w/v is 0.001%-1%; in certain embodiments, the w/v is 0.001%-0.5%; in certain embodiments, the w/v is 0.002%-0.05%; in certain embodiments, the w/v is 0.01%-0.5%; and in certain embodiments, the w/v is 0.01%-0.05%. The concentration of the above-mentioned lyophilized preparation refers to the concentration of active ingredients in an aqueous solution formulated before being placed in a lyophilizer.

The composition of the present disclosure is a sterile lyophilized powder for injection or a solution for injection.

Where the composition of the present disclosure is a sterile lyophilized powder for injection, the pH value refers to a pH value of an aqueous solution formulated before being placed in a lyophilizer.

With regard to the composition of the present disclosure, a single-dose active substance content is 0.01 mg-5 mg.

In addition to an active substance, i.e., a compound of formula (I), and a pH regulator, the composition of the present disclosure may further contain a stabilizer.

The stabilizer can be selected from polyhydroxy compounds, such as sugar, sugar alcohol and polyol; the sugar includes but is not limited to monosaccharide or disaccharide, such as glucose, trehalose, raffinose or sucrose; the sugar alcohol includes but is not limited to mannitol, sorbitol or inositol; and the polyol includes but is not limited to glycerol or propylene glycol or a mixture thereof.

Where the composition is a sterile lyophilized powder for injection, the stabilizer thereof can also be one or any combination of the following polymers, such as HES (isethionic acid), PVP (polyvinylpyrrolidone), PEG (polyethylene glycol), glucan and albumin; the stabilizer can also be selected from a surfactant, such as Tween-80 and Tween-20, or amino acids, such as L-serine, sodium glutamate, alanine and glycine; and the stabilizer can further be selected from a non-aqueous solvent, such as glycerol, dimethyl sulfoxide and tert-butanol.

In certain embodiments, the polyhydroxy compounds are selected from mannitol or propylene glycol.

The concentration of the stabilizer accounts for 0%-20% (w/v) of the total solution; in certain embodiments, the concentration of the stabilizer accounts for 0%-10% (w/v) of the total solution; in certain embodiments, the concentration of the stabilizer accounts for 0%-5% (w/v) of the total solution; in certain embodiments, the concentration of the stabilizer accounts for 0%-1% (w/v) of the total solution; in certain embodiments, the concentration of the stabilizer accounts for 1%-2% (w/v) of the total solution; in certain embodiments, the concentration of the stabilizer accounts for 2%-5% (w/v) of the total solution; and in certain embodiments, the concentration of the stabilizer accounts for 3%-10% (w/v) of the total solution.

In addition to an active substance, i.e., a compound of formula (I), and a pH regulator, the composition can further contain an isotonic regulator, and the isotonic regulator can be selected from glycerol, sodium chloride, sugars, sugar alcohol; the sugars are selected from but not limited to glucose, fructose, maltose, etc.; the sugar alcohol is selected from but not limited to sorbitol, xylitol, mannitol, etc.; in certain embodiments, the isotonic regulator is selected from mannitol, glucose, trehalose or sodium chloride; and in certain embodiments, the isotonic regulator is selected from mannitol.

The weight/volume (w/v) of the isotonic regulator is 0%-10%; in certain embodiments, the w/v is 0%-5%; in certain embodiments, the w/v is 0%-1%; in certain embodiments, the w/v is 1%-2%; and in certain embodiments, the w/v is 2%-5%.

In addition to an active substance, i.e., a compound of formula (I), and a pH regulator, the composition of the present disclosure can further contain an antioxidant, and the antioxidant can be selected from sodium pyrosulfite (which can also be used as an antibacterial agent), sodium sulfite, sodium hydrogen sulfite, potassium metabisulfite, sodium thiosulphate, edetate disodium (which can also be used as an antibacterial agent), calcium disodium edetate (which can also be used as an antibacterial agent), etc.

The weight/volume (w/v) of the antioxidant is 0-2%; in certain embodiments, the weight/volume (w/v) of the antioxidant is 0%-1%; in certain embodiments, the weight/volume (w/v) of the antioxidant is 0%-0.5%; in certain embodiments, the weight/volume (w/v) of the antioxidant is 0.001%-1%; and in certain embodiments, the weight/volume (w/v) of the antioxidant is 0.001%-0.05%.

In addition to an active substance, i.e., a compound of formula (I), and a pH regulator, the composition of the present disclosure may further contain an antibacterial agent, and the antibacterial agent can be selected from sodium pyrosulfite (which can also be used as an antioxidant), edetate disodium (which can also be used as an antioxidant), calcium disodium edetate (which can also be used as an antioxidant), methyl benzoate, sodium octanoate, cresol, benzyl alcohol, phenol, sodium benzoate, phenethyl alcohol, chlorobutanol, phenylethanol, methyl hydroxybenzoate, propyl hydroxybenzoate, etc.; and in certain embodiments, the antibacterial agent is selected from edetate disodium.

The weight/volume (w/v) of the antibacterial agent is 0-2%; in certain embodiments, the weight/volume (w/v) of the antibacterial agent is 0.001%-1%; in certain embodiments, the weight/volume (w/v) of the antibacterial agent is 0.001%-0.005%; and in certain embodiments, the weight/volume (w/v) of the antibacterial agent is 0%-0.005%.

In addition to an active substance, i.e., a compound of formula (I), and a pH regulator, the composition of the present disclosure may contain all of or one or more of an isotonic regulator, an antioxidant, a stabilizer and an antibacterial agent, or none of them are present in the composition of the present disclosure. In addition to these, the composition may also contain other excipients suitable for aqueous solution preparations.

Where the composition is a sterile lyophilized powder for injection, in addition to an active substance, i.e., a compound of formula (I), and a pH regulator, the composition of the present disclosure may further contain a filler. The filler can be selected from one or any combination of trehalose, lactose, sucrose, glucose, mannitol, glucan, sodium dihydrogen phosphate, sodium chloride, disodium hydrogen phosphate, cysteine, glycine, sorbitol, calcium lactobionate, dextran, polyvinylpyrrolidone, cyclodextrin derivatives (such as hydroxypropyl-β-cyclodextrin). In certain embodiments, the filler is selected from one or any combination of trehalose, mannitol and glucose. In certain embodiments, the filler is selected from trehalose.

The weight/volume (w/v) of the filler is 0%-20%; in certain embodiments, the weight/volume (w/v) of the filler is 0%-10%; in certain embodiments, the weight/volume (w/v) of the filler is 0%-5%; and in certain embodiments, the weight/volume percentage (w/v) of the filler is 1%-5%.

The composition of the present disclosure is an aqueous solution preparation or a sterile lyophilized powder for injection and is administered by intravenous injection or infusion. The pH value of the solution is 3-5.5. The composition contains 0.001% w/v-0.5% w/v of an active substance, i.e., a compound of formula (I), an appropriate amount of a pH regulator, 0% w/v-20% w/v of a stabilizer, 0% w/v-10% w/v of an isotonic regulator, 0-2% w/v of an antioxidant, 0-2% w/v of an antibacterial agent, and 0% w/v-20% w/v of a filler. In certain embodiments, the composition contains 0.01% w/v-0.05% w/v of an active substance, i.e., a compound of formula (I), an appropriate amount of a pH regulator, 0% w/v-10% w/v of a stabilizer, 0% w/v-5% w/v of an isotonic regulator, 0.001% w/v-1% w/v of an antioxidant, 0.001% w/v-1% w/v of an antibacterial agent, and 0% w/v-10% w/v of a filler. In certain embodiments, the composition contains 0.01% w/v-0.05% w/v of an active substance, i.e., a compound of formula (I), an appropriate amount of a pH regulator, 0% w/v-10% w/v of a stabilizer, 0% w/v-5% w/v of an isotonic regulator, 0.001% w/v-1% w/v of an antioxidant, 0-0.005% w/v of an antibacterial agent, and 0% w/v-5% w/v of a filler. In certain embodiments, the composition contains 0.001% w/v-0.5% w/v of an active substance, i.e., a compound of formula (I) and an appropriate amount of a pH regulator. In certain embodiments, the composition contains 0.002% w/v-0.05% w/v of an active substance, i.e., a compound of formula (I) and an appropriate amount of a pH regulator.

The "w/v" content of each component in the present disclosure refers to the weight/volume percentage content, i.e., "weight of each component (g)/volume of the solution prior to dispensing (ml)".

The present disclosure further provides a method for preparing the composition, the method comprising the following steps:

(1) dissolving ingredients, other than an active substance, in water for injection;

(2) adding the active substance to the solution obtained in step (1); and (3) adding water to a constant volume, carrying out sterilizing filtration through a 0.22 μm filter, filling and sealing.

The present disclosure further provides a method for preparing the composition, the method comprising the following steps:

(1) dissolving the pH regulator, the isotonic regulator, the antioxidant, the stabilizer, the antibacterial agent and the filler to water for injection;

(2) adding the active substance to the solution obtained in step (1); and (3) adding water to a constant volume, carrying out sterilizing filtration through a 0.22 μm filter, filling and sealing.

The present disclosure further provides a method for preparing the composition, the method comprising the following steps:

(1) dissolving the pH regulator, the isotonic regulator, the antioxidant, the stabilizer, the antibacterial agent and the filler (suitable for a lyophilized preparation) to water for injection, and then adding the active substance, wherein the pH regulator is a buffer solution consisting of a weak acid and a corresponding salt thereof, and the amount of the pH regulator is calculated based on the pH value of the solution reaching 3-5.5;

the composition may contain all of or one or several of the isotonic regulator, antioxidant, stabilizer, antibacterial agent and filler, or none of them are contained in the composition; in certain embodiments, the composition merely contains a pH regulator, such as an acetic acid-sodium acetate buffer; in certain embodiments, the composition contains a pH regulator and a stabilizer, such as acetic acid-sodium acetate and mannitol; where the composition is a sterile lyophilized powder for injection, a filler may be present in the composition;

the volume of water for injection is generally 40%-90% of the total volume, and finally a constant volume is achieved by adding water for injection; and (2) adding water to a constant volume, carrying out sterilizing filtration through a 0.22 μm filter, filling and sealing.

A solution preparation is prepared, and an injection can be obtained by filling and sealing; alternatively, the solution preparation can also be further lyophilized and prepared into a sterile lyophilized powder for injection.

The composition of the present disclosure can also be prepared according to the following preparation method, which comprises the following steps:

(1) dissolving ingredients, other than an active substance, in water for injection;

(2) adding the active substance to the solution obtained in step (1);

(3) adjusting the pH value with the pH regulator to a range of 3.0-5.5; and (4) adding water to a constant volume, carrying out sterilizing filtration through a 0.22 μm filter, filling and sealing.

The composition of the present disclosure can also be prepared according to the following preparation method, which comprises the following steps:

(1) dissolving the pH regulator, the isotonic regulator, the antioxidant, the stabilizer, the antibacterial agent and the filler to water for injection;

(2) adding the active substance to the solution obtained in step (1);

(3) adjusting the pH value with the pH regulator to a range of 3.0-5.5; and (4) adding water to a constant volume, carrying out sterilizing filtration through a 0.22 μm filter, filling and sealing.

The composition of the present disclosure can also be prepared according to the following preparation method, which comprises the following steps:

(1) dissolving the pH regulator, the isotonic regulator, the antioxidant, the stabilizer, the antibacterial agent and the filler (suitable for a lyophilized preparation) to water for injection;

(2) adding the active substance to the solution obtained in step (1);

(3) determining the pH value of the solution obtained in step (2), and based on the pH value, selecting one of the pH regulator components to adjust the pH value of the solution to 3-5.5; and (4) adding water to a constant volume, carrying out sterilizing filtration through a membrane filter (such as 0.22 μm), filling and sealing.

A solution preparation is prepared, and an injection can be obtained by filling and sealing; alternatively, the solution preparation can also be further lyophilized and prepared into a sterile lyophilized powder for injection.

The solution preparation can be filled and sealed in pyrogen-free vials, such as penicillin vials and ampoule vials. The volume of pyrogen-free vials can be 1-10 mL, such as 1 ml, 2 ml, 3 ml, 5 mL, 7 mL, and 10 mL.

Where the composition of the present disclosure is a sterile lyophilized powder for injection, and on the basis of a solution preparation, a lyophilizing step is further comprised.

In certain embodiments, the lyophilizing step comprises:

(1) pre-freezing;

(2) cooling partition boards to −35° C. or lower and maintaining for 1-2 h; then cooling a chamber to −50° C. or lower and vacuuming to 20 Pa or lower; opening a limited leakage valve; raising the temperature to −5° C. over 3-5 h and maintaining for another 1-3 h; raising the temperature to 10° C. over 2-4 h and maintaining until the temperature of the preparation reaches 0° C. or higher; raising the temperature to 35° C. over 2-3 h and maintaining until the temperature of the preparation reaches 25° C. or higher; and then closing the limited leakage valve and maintaining the temperature for 1-3 h; and (3) vacuuming or charging nitrogen, completely stoppering, and then taking out from the chamber and capping.

In certain embodiments, the lyophilizing step comprises:

(1) pre-freezing;

the solution that has been subjected to sterilizing filtration through a membrane filter (such as 0.22 μm) was dispensed into penicillin vials with suitable sizes (such as the size designation of 3 mL) according to a specified amount such as 1 mL, and the vials were partially stoppered and placed in a lyophilizer for pre-freezing;

(2) carrying out a lyophilizing process: cooling partition boards to −35° C. or lower and maintaining for 1-2 h; then cooling a chamber to −50° C. or lower and vacuuming to 20 Pa or lower; opening a limited leakage valve; raising the temperature to −5° C. over 3-5 h and maintaining for another 1-3 h; raising the temperature to 10° C. over 2-4 h and maintaining until the temperature of the preparation reaches 0° C. or higher; raising the temperature to 35° C. over 2-3 h and maintaining until the temperature of the preparation reaches 25° C. or higher; and then closing the limited leakage valve and maintaining the temperature for 1-3 h; and (3) vacuuming or charging nitrogen, completely stoppering, and then taking out from the chamber and capping.

The preparation method of the sterile lyophilized powder for injection of the present disclosure is simple and easy to implement, facilitates long-term storage and convenient transportation, and is beneficial to large-scale production.

The present disclosure also relates to a method for treating or preventing a disease or condition associated with kappa opioid receptors in a mammal, wherein the method comprises administering the composition of the present disclosure.

In certain embodiments, the disease or condition associated with kappa opioid receptors is selected from the group consisting of pain, inflammation, itching, edema, hyponatremia, hypokalemia, intestinal obstruction, cough and glaucoma.

In certain embodiments, the pain is selected from neuropathic pain, somatic pain, visceral pain and skin pain; in particular, neuropathic pain.

The present disclosure also relates to the use of the composition thereof in the preparation of a medicine for a disease or condition associated with kappa opioid receptors.

In certain embodiments, the disease or condition associated with kappa opioid receptors is selected from pain, inflammation, itching, edema, hyponatremia, hypokalemia, intestinal obstruction, cough and glaucoma.

In certain embodiments, the pain is selected from neuropathic pain, somatic pain, visceral pain and skin pain; in particular, neuropathic pain.

The preparation method of the composition of the present disclosure, especially the aqueous solution injection and the lyophilized powder for injection, is simple and involves no excipients or only a few types and a small amount of excipients, leading to a reduced cost; and the storage stability and safety thereof comply with national standards for drugs, are comparable to commercially available preparations, and are suitable for clinical applications.

Unless stated to the contrary, the terms used in the description and claims have the following meanings.

The carbon, hydrogen, oxygen, sulfur, nitrogen or halogen involved in the groups and compounds of the present disclosure all comprises their isotopes, and the carbon, hydrogen, oxygen, sulfur, nitrogen or halogen involved in the groups and compounds of the present disclosure is optionally further substituted with one or more of their corresponding isotopes, wherein the isotopes of carbon comprise $^{12}C$, $^{13}C$ and $^{14}C$, the isotopes of hydrogen comprise protium (H), deuterium (D, also known as heavy hydrogen), and tritium (T, also known as superheavy hydrogen), the isotopes of oxygen comprise $^{16}O$, $^{17}O$ and $^{18}O$, the isotopes of sulfur comprise $^{32}S$, $^{33}S$, $^{34}S$ and $^{36}S$, the isotopes of nitrogen comprise $^{14}N$ and $^{15}N$, the isotopes of fluorine comprise $^{19}F$, the isotopes of chlorine comprise $^{35}Cl$ and $^{37}Cl$, and the isotopes of bromine comprise $^{79}Br$ and $^{11}Br$.

An "alkyl" means a straight or branched chain monovalent saturated hydrocarbon group, with a main chain comprising 1 to 10 carbon atoms, preferably 1 to 8 carbon atoms, further preferably 1 to 6 carbon atoms, more preferably 1 to 4 carbon atoms, and most preferably 1 to 2 carbon atoms. Examples of alkyl include, but are not limited to, methyl, ethyl, n-propyl, isopropyl, n-butyl, isobutyl, sec-butyl, tertbutyl, n-pentyl, 2-pentyl, 3-pentyl, 2-methyl-2-butyl, 3-methyl-2-butyl, n-hexyl, n-heptyl, n-octyl, n-nonyl, n-decyl, etc. The alkyl can be optionally further substituted with 0, 1, 2, 3, 4 or 5 substituents selected from F, Cl, Br, I, =O, hydroxyl, $—SR^{19}$, nitro, cyano, $C_{1-6}$alkyl, $C_{1-6}$hydroxylalkyl, $C_{1-6}$alkoxy, $C_{2-6}$alkenyl, $C_{2-6}$alkynyl, $C_{3-8}$carbocyclyl, 3- to 8-membered heterocyclyl, $—(CH_2)_a—C(=O)—R^{19}$, $—(CH_2)_k—C(=O)—O—R^{19}$, $—(CH_2)_k—C(=O)—NR^{19}R^{19a}$, $—(CH_2)_k—S(=O)_j—R^{19}$, $—O—C(=O)—O—R^{19}$ or $—NR^{19}R^{19a}$, wherein $R^{19}$ and $R^{19a}$ are each independently selected from H, hydroxyl, amino, carboxyl, $C_{1-6}$alkyl, $C_{1-8}$alkoxy, $C_{2-8}$alkenyl, $C_{2-8}$alkynyl, 3- to 10-membered carbocyclyl, 4- to 10-membered heterocyclyl, 3- to 10-membered carbocyclyloxy or 4- to 10-membered heterocyclyloxy, a is selected from 0, 1, 2 or 3, k is selected from 0, 1, 2, 3, 4 or 5, and j is selected from 0, 1 or 2. The "alkyl", "a", "k", "j", "$R^{19}$" and "$R^{19a}$" herein are as defined above.

An "alkylene" means a straight or branched chain divalent saturated hydrocarbon group, including $—(CH_2)_v—$ (v is an integer from 1 to 10), and examples of alkylene include, but are not limited to, methylene, ethylene, propylene, butylene, etc. The alkylene may be optionally further substituted with 0, 1, 2, 3, 4 or 5 substituents selected from F, Cl, Br, I, =O, hydroxyl, $—SR^{19}$, nitro, cyano, $C_{1-6}$alkyl, $C_{1-6}$hydroxylalkyl, $C_{1-6}$alkoxy, $C_{2-6}$alkenyl, $C_{2-6}$alkynyl, $C_{3-8}$carbocyclyl, 3- to 8-membered heterocyclyl, $—(CH_2)_a—C(=O)—R^{19}$, $—(CH_2)_k—C(=O)—O—R^{19}$, $—(CH_2)_k—C(=O)—NR^{19}R^{19a}$, $—(CH_2)_k—S(=O)_j—R^{19}$, $—O—C(=O)—O—R^{19}$ or $—NR^{19}R^{19a}$ When the number of substituents in the alkylene is 2 or more, the substituents may be fused together to form a cyclic structure. The "alkylene" herein is as defined above.

An "alkoxy" means a monovalent group of O-alkyl, wherein the alkyl is as defined herein, and examples of alkoxy include, but are not limited to methoxy, ethoxy, 1-propoxy, 2-propoxy, 1-butoxy, 2-methyl-1-propoxy, 2-butoxy, 2-methyl-2-propoxy, 1-pentyloxy, 2-pentyloxy, 3-pentyloxy, 2-methyl-2-butoxy, 3-methyl-2-butoxy, 3-methyl-1-butoxy, 2-methyl-1-butoxy, etc.

An "alkenyl" means a straight or branched chain monovalent unsaturated hydrocarbon group having at least 1, usually 1, 2 or 3 carbon-carbon double bonds, with a main chain comprising 2 to 10 carbon atoms, further preferably 2 to 6 carbon atoms, more preferably 2 to 4 carbon atoms. Examples of alkenyl include, but are not limited to vinyl, allyl, 1-propenyl, 2-propenyl, 1-butenyl, 2-butenyl, 3-butenyl, 1-pentenyl, 2-pentenyl, 3-pentenyl, 4-pentenyl, 1-methyl-1-butenyl, 2-methyl-1-butenyl, 2-methyl-3-butenyl, 1-hexenyl, 2-hexenyl, 3-hexenyl, 4-hexenyl, 5-hexenyl, 1-methyl-1-pentenyl, 2-methyl-1-pentenyl, 1-heptenyl, 2-heptenyl, 3-heptenyl, 4-heptenyl, 1-octenyl, 3-octenyl, 1-nonenyl, 3-nonenyl, 1-decenyl, 4-decenyl, 1,3-butadiene, 1,3-pentadiene, 1,4-pentadiene, 1,4-hexadiene, etc. The alkenyl may be optionally further substituted with 0, 1, 2, 3, 4 or 5 substituents selected from F, Cl, Br, I, =O, hydroxyl, $—SR^{19}$, nitro, cyano, $C_{1-6}$alkyl, $C_{1-6}$hydroxylalkyl, $C_{1-6}$alkoxy, $C_{2-6}$alkenyl, $C_{2-6}$alkynyl, $C_{3-8}$carbocyclyl, 3- to 8-membered heterocyclyl, $—(CH_2)_a—C(=O)—R^{19}$, $—(CH_2)_k—C(=O)—O—R^{19}$, $—(CH_2)_k—C(=O)—NR^{19}R^{19a}$, $—(CH_2)_k—S(=O)_j—R^{19}$, $—O—C(=O)—O—R^{19}$ or $—NR^{19}R^{19a}$. The "alkenyl" herein is as defined above.

An "alkynyl" means a straight or branched chain monovalent unsaturated hydrocarbon group having at least 1, usually 1, 2 or 3 carbon-carbon triple bonds, with a main chain comprising 2 to 10 carbon atoms, further preferably 2 to 6 carbon atoms, more preferably 2 to 4 carbon atoms. Examples of alkynyl include, but are not limited to ethynyl, 1-propynyl, 2-propynyl, butynyl, 2-butynyl, 3-butynyl, 1-methyl-2-propynyl, 4-pentynyl, 3-pentynyl, 1-methyl-2-butynyl, 2-hexynyl, 3-hexynyl, 2-heptynyl, 3-heptynyl, 4-heptynyl, 3-octynyl, 3-nonynyl, 4-decynyl, etc. The alkynyl may be optionally further substituted with 0, 1, 2, 3, 4 or 5 substituents selected from F, Cl, Br, I, =O, hydroxyl, $—SR^{19}$, nitro, cyano, $C_{1-6}$alkyl, $C_{1-6}$hydroxylalkyl, $C_{1-6}$alkoxy, $C_{2-6}$alkenyl, $C_{2-6}$alkynyl, $C_{3-8}$carbocyclyl, 3- to 8-membered heterocyclyl, $—(CH_2)_a—C(=O)—R^{19}$, $—(CH_2)_k—C(=O)—O—R^{19}$, $—(CH_2)_k—C(=O)—NR^{19}R^{19a}$, $—(CH_2)_k—S(=O)_j—R^{19}$, $—O—C(=O)—O—R^{19}$ or $—NR^{19}R^{19a}$. The "alkynyl" herein is as defined above.

A "cycloalkyl" means a monovalent saturated carbocyclic hydrocarbon group, usually having from 3 to 10 carbon atoms, and non-limiting examples include cyclopropyl, cyclobutyl, cyclopentyl, cyclohexyl, cycloheptyl, etc. The cycloalkyl may be optionally further substituted with 0, 1, 2, 3, 4 or 5 substituents selected from F, Cl, Br, I, =O, hydroxyl, $—SR^{19}$, nitro, cyano, $C_{1-6}$alkyl, $C_{1-6}$hydroxylalkyl, $C_{1-6}$alkoxy, $C_{2-6}$alkenyl, $C_{2-6}$alkynyl, $C_{3-8}$carbocyclyl, 3- to 8-membered heterocyclyl, $—(CH_2)_a—C(=O)—R^{19}$, $—(CH_2)_k—C(=O)—O—R^{19}$, $—(CH_2)_k—C(=O)—NR^{19}R^{19a}$, $—(CH_2)_k—S(=O)_j—R^{19}$, $—O—C(=O)—O—R^{19}$ or $—NR^{19}R^{19a}$. The "cycloalkyl" herein is as defined above.

A "carbocyclic" or "carbocyclyl" means an aromatic ring or a saturated or unsaturated non-aromatic ring. The aromatic or non-aromatic ring may be, but is not limited to, a 3- to 10-membered monocyclic ring, a 4- to 12-membered bicyclic ring or a 10- to 15-membered tricyclic ring system. The carbocyclyl may be substituted with substituents, any two of which together with the atom to which they are attached form a monocyclic, fused, bridged, or spiro ring, and the substituents can be selected from a monocyclic, fused, bridged, or spiro ring; and non-limiting examples include cyclopropyl, cyclobutyl, cyclopentyl, 1-cyclopentyl-1-alkenyl, 1-cyclopentyl-2-alkenyl, 1-cyclopentyl-3-alkenyl, cyclohexyl, 1-cyclohexyl-2-alkenyl, 1-cyclohexyl-3-alkenyl, cyclohexenyl, cyclohexadienyl, cycloheptyl, cyclooctyl, cyclononyl, cyclodecyl, cycloundecyl, cyclododecyl, phenyl or naphthyl. The carbocyclyl can be optionally further substituted with 0, 1, 2, 3, 4 or 5 substituents selected from F, Cl, Br, I, =O, hydroxyl, $—SR^{19}$, nitro, cyano, $C_{1-6}$alkyl, $C_{1-6}$hydroxylalkyl, $C_{1-6}$alkoxy, $C_{2-6}$alkenyl, $C_{2-6}$alkynyl, $C_{3-8}$carbocyclyl, 3- to 8-membered heterocyclyl, $—(CH_2)_a—C(=O)—R^{19}$, $—(CH_2)_k—C(=O)—O—R^{19}$, $—(CH_2)_k—C(=O)—NR^{19}R^{19a}$, $—(CH_2)_k—S(=O)_j—R^{19}$, $—O—C(=O)—O—R^{19}$ or $—NR^{19}R^{19a}$. The "carbocyclic" or "carbocyclyl" herein is as defined above.

A "heterocycle" or "heterocyclyl" means an aromatic ring or a saturated or unsaturated non-aromatic ring that contains heteroatom(s); and the aromatic or non-aromatic ring may be a 3- to 10-membered monocyclic system, a 4- to 12-membered bicyclic system or a 10- to 15-membered tricyclic system, and comprises 1 to 4 heteroatoms selected from N, O or S, preferably a 3- to 8-membered heterocyclyl, wherein optionally substituted N and S in the ring of the heterocyclyl may be oxidized to various oxidation states. The heterocyclyl may be linked to other groups (such as a group on the parent nucleus or a substituent of the heterocyclyl) via the heteroatom or carbon atom on the heterocyclyl. The heterocyclyl may be substituted with substituents, any two of which together with the atom to which they are attached form a monocyclic, fused, bridged, or spiro ring, and the substituents can be selected from a monocyclic, fused, bridged, or spiro ring; and non-limiting examples include epoxyethyl, epoxypropyl, azacyclopropyl, oxacyclobutyl, azacyclobutyl, thioheterobutyl, 1,3-dioxolanyl, 1,4-dioxolanyl, 1,3-dioxohexyl, azacycloheptyl, oxepanyl, thiocycloheptyl, oxazepinyl, diazepinyl, thiazepinyl, pyridyl, piperidinyl, homopiperidinyl, furyl, thienyl, pyranyl, N-alkylpyrrolyl, pyrimidinyl, pyrazinyl, pyridazinyl, piperazinyl, homopiperazinyl, imidazolyl, morpholinyl, thiomorpholinyl, oxathianyl, dihydrofuranyl, dihydropyranyl, dithiapentanyl, tetrahydrofuranyl, tetrahydrothienyl, tetrahydropyranyl, tetrahydrothyranyl, tetrahydropyrrolyl, tetrahydroimidazolyl, tetrahydrothiazolyl, tetrahydropyranyl, benzimidazolyl, benzopyridyl, pyrrolopyridyl, benzodihydrofuryl, 2-pyrrolinyl, 3-pyrrolinyl, dihydroindolyl, 2H-pyranyl, 4H-pyranyl, dioxane, 1,3-dioxolyl, pyrazolinyl, dithiaalkyl, dithiacenyl, dihydrothienyl, pyrazolidinyl, imidazolinyl, imidazolidinyl, 1,2,3,4-tetrahydroisoquinolinyl, 3-azabicyclo[3.1.0]hexyl, 3-azabicyclo[4.1.0]heptyl, azabicyclo[2.2.2]hexyl, 3H-indolylquinazinyl, N-pyridyl urea, 1,1-dioxothiomorpholinyl, azabicyclo[3.2.1]octyl, azabicyclo[5.2.0]nonanyl, oxatricyclo[5.3.1.1]dodecyl, azaadamantyl and oxaspiro[3.3]heptyl. The heterocyclyl can be optionally further substituted with 0, 1, 2, 3, 4 or 5 substituents selected from F, Cl, Br, I, =O, hydroxyl, —$SR^{19}$, nitro, cyano, $C_{1-6}$alkyl, $C_{1-6}$hydroxylalkyl, $C_{1-6}$alkoxy, $C_{2-6}$alkenyl, $C_{2-6}$alkynyl, $C_{3-8}$carbocyclyl, 3- to 8-membered heterocyclyl, —$(CH_2)_a$—C(=O)—$R^{19}$, —$(CH_2)_k$—C(=O)—O—$R^{19}$, —$(CH_2)_k$—C(=O)—$NR^{19}R^{19a}$, —$(CH_2)_k$—S(=O)$_j$—$R^{19}$, —O—C(=O)—O—$R^{19}$ or —$NR^{19}R^{19a}$. The "heterocycle" or "heterocyclyl" herein is defined as described above.

A "bridged ring" or "bridged ring group" means a polycyclic group containing any two carbon atoms that are not directly linked, which may contain 0 or more double bonds and can be substituted or unsubstituted; any ring in the bridged ring system may contain 0 to 5 heteroatoms or groups selected from N, S(=O)$_n$ or O (wherein n is 0, 1 or 2). The ring atoms contain 5 to 20 atoms, preferably 5 to 14 atoms, further preferably 5 to 12 atoms, and still further preferably 5 to 10 atoms. Non-limiting examples include

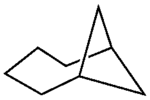, 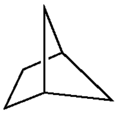, 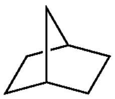,

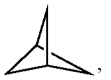, 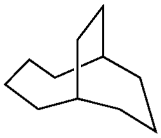, 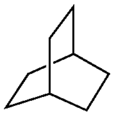,

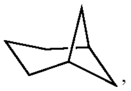, 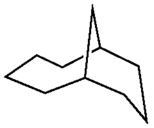, 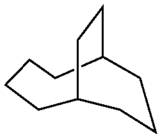,

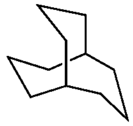, 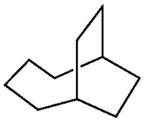, 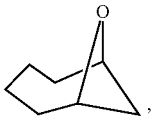,

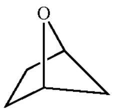, 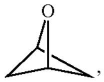, 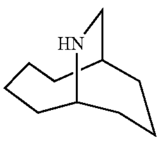,

-continued

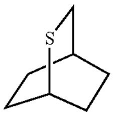, 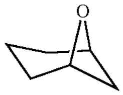, 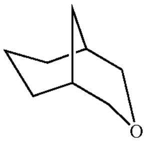,

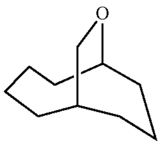, 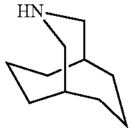, 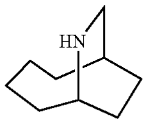,

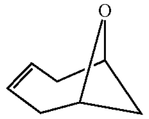, 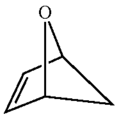, 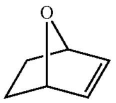,

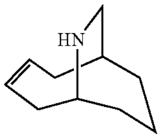, 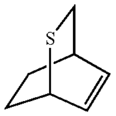, 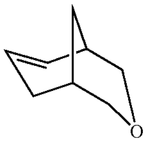,

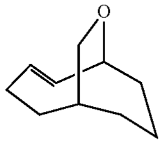, 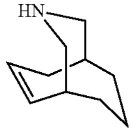, 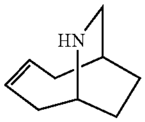,

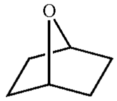, 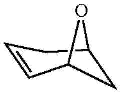

and adamantane. When the bridged ring or bridged ring group is substituted, the substituents are 1 to 5 groups selected from F, Cl, Br, I, alkyl, cycloalkyl, alkoxy, haloalkyl, mercaptan, hydroxyl, nitro, sulfhydryl, amino, cyano, isocyano, aryl, heteroaryl, heterocyclyl, bridged ring group, spiro ring group, fused ring group, hydroxylalkyl, =O, carbonyl, aldehyde, carboxylic acid, carboxylic ester, —$(CH_2)_m$—C(=O)—$R^a$, —O—$(CH_2)_m$—C(=O)—$R^a$, —$(CH_2)_m$—C(=O)—$NR^bR^c$, —$(CH_2)_m$S(=O)$_n$$R^a$, —$(CH_2)_m$-alkenyl-$R^a$, $OR^d$ or —$(CH_2)_m$-alkynyl-$R^a$ (wherein m and n are 0, 1 or 2), arylthio, thiocarbonyl, silyl or —$NR^bR^c$, wherein $R^b$ and $R^c$ are independently selected from H, hydroxyl, amino, carbonyl, alkyl, alkoxy, cycloalkyl, heterocyclyl, aryl, heteroaryl, sulfonyl, trifluoromethylsulfonyl. Alternatively, $R^b$ and $R^c$ may form a five- or six-membered cycloalkyl or heterocyclyl. $R^a$ and $R^d$ are each independently selected from aryl, heteroaryl, alkyl, alkoxy, cycloalkyl, heterocyclyl, carbonyl, ester group, bridged ring group, spiro ring group or fused ring group.

A "spiro ring" or "spiro ring group" means a 5- to 20-membered polycyclic group sharing one carbon atom (referred to as a spiro atom) between substituted or unsubstituted monocyclic rings, which may contain 0 to 5 double bonds, and may contain 0 to 5 heteroatoms selected from N, O or S(=O)$_n$. The spiro ring or spiro ring group is preferably 6- to 14-membered, further preferably 6- to 12-membered, and more preferably 6- to 10-membered spiro ring or spiro ring group; and non-limiting examples include

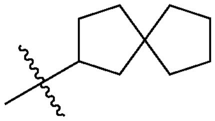 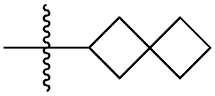

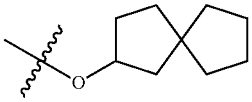 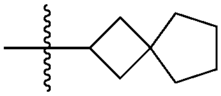

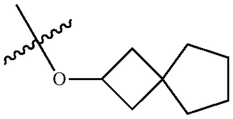 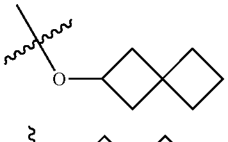

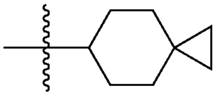 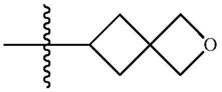

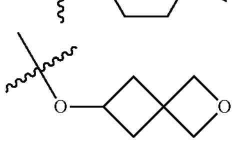 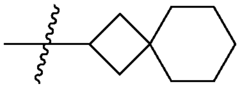

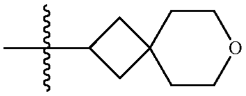 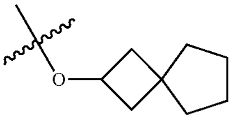

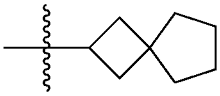 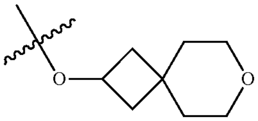

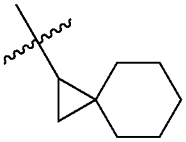 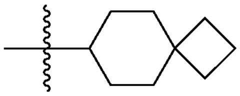

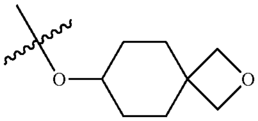 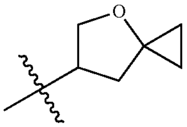

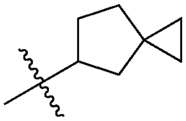 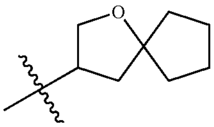

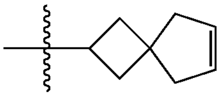 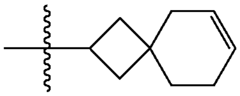

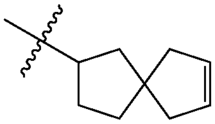 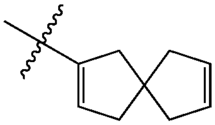

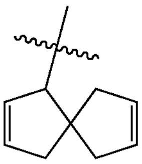 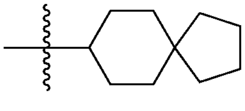

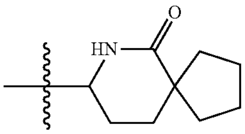 and

-continued

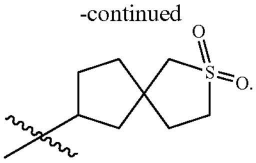

When the spiro ring or spiro ring group is substituted, the substituents are 1 to 5 groups selected from F, Cl, Br, I, alkyl, cycloalkyl, alkoxy, haloalkyl, mercaptan, hydroxyl, nitro, sulfhiydryl, amino, cyano, isocyano, aryl, heteroaryl, heterocyclyl, bridged ring group, spiro ring group, fused ring group, hydroxylalkyl, ═O, carbonyl, aldehyde, carboxylic acid, carboxylic ester, —$(CH_2)_m$—C(═O)—$R^a$, —O—$(CH_2)_m$—C(═O)—$R^a$, —$(CH_2)_m$—C(═O)—$NR^bR^c$, —$(CH_2)_m$S(═O)$_n$ $R^a$, —$(CH_2)_m$-alkenyl-$R^a$, $OR^d$ or —$(CH_2)_m$-alkynyl-$R^a$ (wherein m and n are 0, 1 or 2), arylthio, thiocarbonyl, silyl or —$NR^bR^c$, wherein $R^b$ and $R^c$ are independently selected from H, hydroxyl, amino, carbonyl, alkyl, alkoxy, cycloalkyl, heterocyclyl, aryl, heteroaryl, sulfonyl, trifluoromethylsulfonyl. Alternatively, $R^b$ and $R^c$ may form a five- or six-membered cycloalkyl or heterocyclyl. $R^a$ and $R^d$ are each independently selected from aryl, heteroaryl, alkyl, alkoxy, cycloalkyl, heterocyclyl, carbonyl, ester group, bridged ring group, spiro ring group or fused ring group.

A "fused ring" or "fused ring group" refers to a polycyclic group in which each ring in the system shares an adjacent pair of carbon atoms with other rings in the system, wherein one or more rings may contain 0 or more double bonds, which may be substituted or unsubstituted, and each ring in the fused ring system may contain 0 to 5 heteroatoms selected from N, S(═O)n or O. The fused ring or fused ring group is preferably 5- to 20-membered, further preferably 5- to 14-membered, more preferably 5- to 12-membered, and still further preferably 5- to 10-membered fused ring or fused ring group; and non-limiting examples include

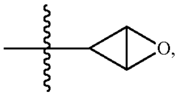 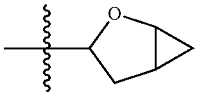,

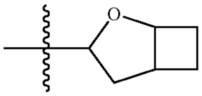, 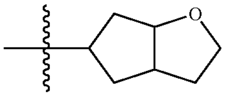,

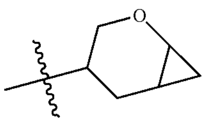, 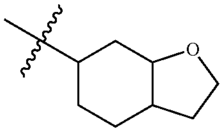,

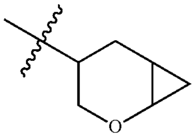, 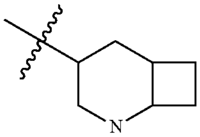,

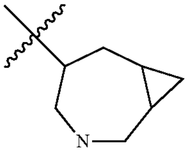, 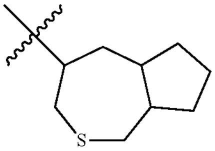,

-continued

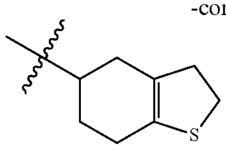,
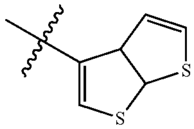,
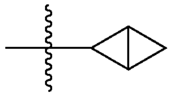,
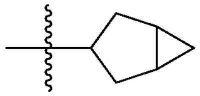,
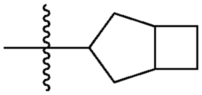,
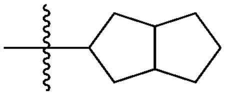,
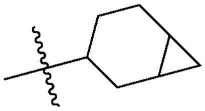,
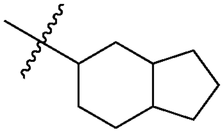,
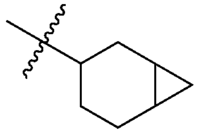,
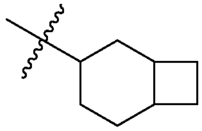,
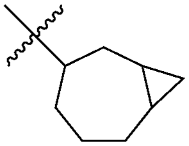,
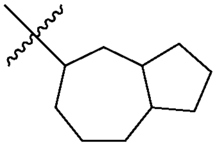,
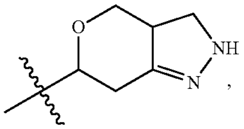,
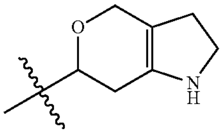,
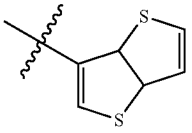
and
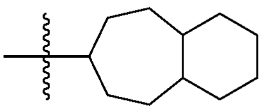.

When the fused ring or fused ring group is substituted, the substituents are 1 to 5 groups selected from F, Cl, Br, I, alkyl, cycloalkyl, alkoxy, haloalkyl, mercaptan, hydroxyl, nitro, sulfhydryl, amino, cyano, isocyano, aryl, heteroaryl, heterocyclyl, bridged ring group, spiro ring group, fused ring group, hydroxylalkyl, =O, carbonyl, aldehyde, carboxylic acid, carboxylic ester, $-(CH_2)_m-C(=O)-R^a$, $-O-(CH_2)_m-C(=O)-R^a$, $-(CH_2)_m-C(=O)-NR^bR^c$, $-(CH_2)_mS(=O)_nR^a$, $-(CH_2)_m$-alkenyl-$R^a$, $OR^d$ or $-(CH_2)_m$-alkynyl-$R^a$ (wherein m and n are 0, 1 or 2), arylthio, thiocarbonyl, silyl or $-NR^bR^c$, wherein $R^b$ and $R^c$ are independently selected from H, hydroxyl, amino, carbonyl, alkyl, alkoxy, cycloalkyl, heterocyclyl, aryl, heteroaryl, sulfonyl, trifluoromethylsulfonyl. Alternatively, $R^b$ and $R^c$ may form a five- or six-membered cycloalkyl or heterocyclyl. $R^a$ and $R^d$ are each independently selected from aryl, heteroaryl, alkyl, alkoxy, cycloalkyl, heterocyclyl, carbonyl, ester group, bridged ring group, spiro ring group or fused ring group.

"Optional" or "optionally" refers to that events or circumstances subsequently described may but not necessarily occur, and the description includes the occasions where the events or circumstances occur or do not occur. For example, "alkyl optionally substituted with F" means that the alkyl may but not necessarily be substituted with F, and the description includes the case where the alkyl is substituted with F and the case where the alkyl is not substituted with F.

On the premise of no contradiction, the above embodiments can be combined with each other arbitrarily.

DETAILED DESCRIPTION OF EMBODIMENTS

The technical solutions of the present disclosure will be described in detail below in conjunction with the drawings and examples, but the protection scope of the present disclosure includes but is not limited thereto.

Unless otherwise specified, tartaric acid is from Merck, Germany.

Example 1 pH Range 750 ml of water for injection was measured and taken; nitrogen was charged beneath the surface of the liquid for about 20 min; and the water temperature was controlled to be 50° C. or less. 37.5 mg of compound II was weighed, added to the above-mentioned water for injection and stirred to dissolution and clarification to obtain solution (1). Solution (1) was adjusted with glacial acetic acid (source: Chengdu Kelong Chemical Co., Ltd.) and tartaric acid to different pH values, respectively, and aqueous solutions containing compound II at different pH values were obtained. The aqueous solutions were placed under the conditions of 40° C.±2° C. for 10 days, and the performance of related substances in the solutions at different pH values was examined (including the solution at a pH value not being adjusted), with data shown in Table 1.

TABLE 1

Examination results of related substances in solutions containing compound II at different pH values

| Sample storage condition | Sample | pH value | Total impurity (%) |
|---|---|---|---|
| 40° C. ± 2° C., 10 days | Compound II solution (at a pH value adjusted with glacial acetic acid) | 2.94 | 0.986 |
| | | 3.99 | 0.490 |
| | | 4.94 | 0.742 |
| | | 6.01 | 1.079 |
| | | 6.97 | 1.588 |
| | | 7.86 | 1.450 |
| | | 9.12 (the solution at a pH value not being adjusted) | 1.586 |
| | Compound II solution (at a pH value adjusted with tartaric acid) | 3.03 | 0.980 |
| | | 3.99 | 0.486 |
| | | 4.79 | 0.702 |
| | | 5.95 | 1.289 |
| | | 6.97 | 1.496 |
| | | 7.86 | 1.580 |
| | | 9.12 (the solution at a pH value not being adjusted) | 1.586 |

Figure 1:
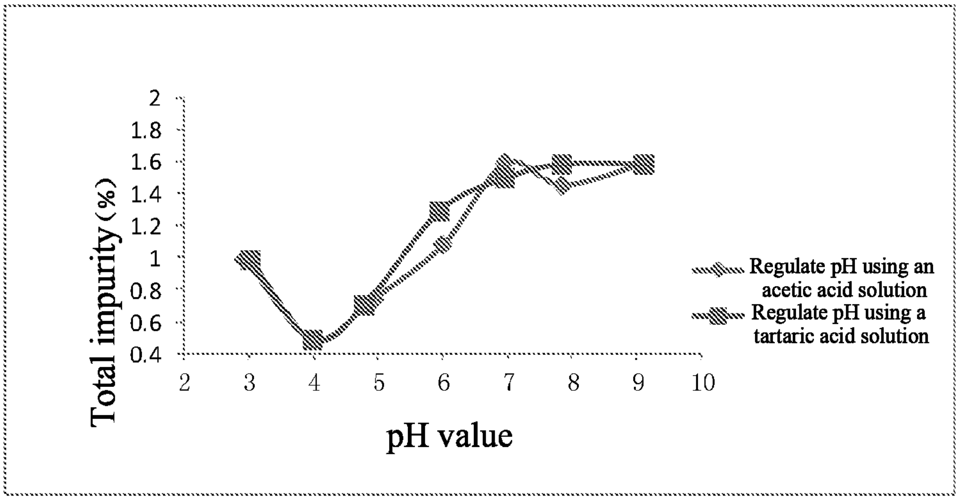
FIG. 1 shows curves of glacial acetic acid or tartaric acid-adjusted pH versus total impurity of compound II solution.

Curves of pH versus total impurity, which are plotted with the data of the pH values and total impurity of compound II solution (at a pH value adjusted with glacial acetic acid) and compound II solution (at a pH value adjusted with tartaric acid) in Table 1 respectively, are shown in FIG. 1. It can be seen from Table 1 and FIG. 1 that the compound II aqueous solutions prepared thereby have the best stability at a pH value of about 4; and related substances in the compound II solutions at a pH value adjusted with glacial acetic acid and tartaric acid show substantially the same trend of changes.

Considering the operability of industrial production, we examined the stability of solutions at a pH range of 3-5.5. 750 ml of water for injection was measured and taken; nitrogen was charged beneath the surface of the liquid for about 20 min; and the water temperature was controlled to be 50° C. or less. 37.5 mg of compound II was weighed, added to the above-mentioned water for injection and stirred to dissolution and clarification to obtain solution (1). Solution (1) was adjusted with glacial acetic acid (source: Chengdu Kelong Chemical Co., Ltd.) to different pH values, and aqueous solutions containing compound II at different pH values were obtained. The aqueous solutions were placed under the conditions of 40° C.±2° C. for 10 days, and the performance of related substances in the solutions at different pH values was examined, with data shown in Table 2.

TABLE 2

Examination results of related substances in solutions containing compound II at different pH values

| Sample storage condition | Sample | pH value | Total impurity (%) |
|---|---|---|---|
| 40° C. ± 2° C., 10 days | Compound II solution (at a pH value adjusted with glacial acetic acid) | 2.98 | 1.005 |
| | | 3.22 | 0.842 |
| | | 3.49 | 0.624 |
| | | 3.74 | 0.537 |
| | | 3.99 | 0.498 |
| | | 4.25 | 0.506 |
| | | 4.48 | 0.602 |
| | | 4.77 | 0.695 |
| | | 5.00 | 0.755 |
| | | 5.24 | 0.866 |
| | | 5.51 | 0.921 |

Figure 2:
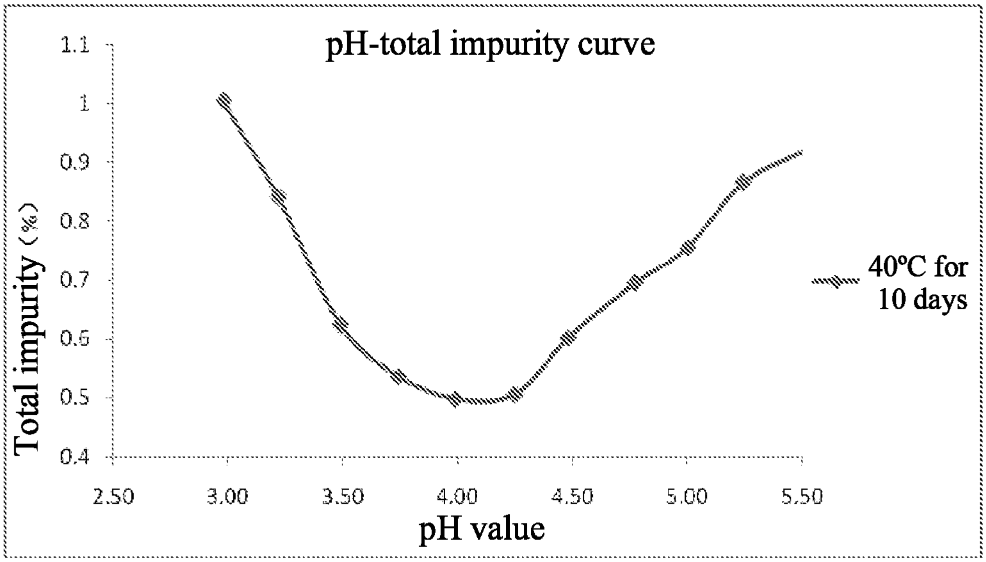
FIG. 2 shows a curve of different pH versus total impurity of compound II solution.

A curve of pH versus total impurity, which is plotted with the data of the pH values and total impurity of compound II solution in Table 2, is shown in FIG. 2. It can be seen from Table 2 and FIG. 2 that this product is stable at a pH range of 3-5.5.

Example 2 Formulation 1

The prescription is as follows:

| Substances | Content |
|---|---|
| Compound II | 0.10 g |
| Glacial acetic acid | 0.525 g |
| Sodium acetate | 0.207 g |
| Water for injection, making up the volume to | 1000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Chengdu Kelong Chemical Co., Ltd.) and sodium acetate (source: Chengdu Jinshan Chemical Test Co., Ltd.) were added to the above-mentioned water for injection under stirring and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing, and formulation 1 solution for injection was obtained.

The sample of Formulation 1 solution for injection was placed under the conditions of 40° C.±2° C. for 5 days; compound II raw material (stored under refrigerated conditions of 2° C.-8° C.) was used as a control; and changes of related substances in the sample were examined, with data shown in Table 3.

TABLE 3

Examination results of related substances of formulation 1 solution for injection

| Sample | Sample storage condition | Total impurity (%) |
|---|---|---|
| Compound II | 0 days | 1.098 |
| Formulation 1 solution for injection | 40° C. ± 2° C., 5 days | 1.164 |

After the sample prepared according to Example 2 was placed at 40° C. 2° C. for high temperature acceleration for 5 days, the total impurity level was not significantly different from that of the raw material at day 0, indicating that formulation 1 has a good stability.

Example 3 Formulation 2

The prescription is as follows:

| Substances | Content |
|---|---|
| Compound II | 0.10 g |
| Glacial acetic acid | 1.050 g |
| Sodium acetate | 0.415 g |
| Water for injection, making up the volume to | 1000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Chengdu Kelong Chemical Co., Ltd.) and sodium acetate (source: Chengdu Jinshan Chemical Test Co., Ltd.) were added to the above-mentioned water for injection under stirring and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing, and formulation 2 solution for injection was obtained.

Formulation 2 solution for injection was placed under the conditions of 40° C. 2° C. for 5 days; compound II raw material (stored under refrigerated conditions of 2° C.-8° C.) was used as a control; and changes of related substances in the sample were examined, with data shown in Table 4.

TABLE 4

| Examination results of related substances of formulation 2 solution for injection | | |
|---|---|---|
| Sample | Sample storage condition | Total impurity (%) |
| Compound II | 0 days | 1.098 |
| Formulation 2 solution for injection | 40° C. ± 2° C., 5 days | 1.132 |

After the sample of formulation 2 solution for injection was placed at 40° C.±2° C. for high temperature acceleration for 5 days, the total impurity level was not significantly different from that of the raw material at day 0, indicating that formulation 2 solution for injection has a good stability.

Example 4 Formulation 3

The prescription is as follows:

| Substances | Content |
|---|---|
| Compound II | 0.10 g |
| Glacial acetic acid | 1.260 g |
| Sodium acetate | 0.518 g |
| Water for injection, making up the volume to | 1000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Chengdu Kelong Chemical Co., Ltd.) and sodium acetate (source: Chengdu Jinshan Chemical Test Co., Ltd.) were added to the above-mentioned water for injection under stirring and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing, and formulation 3 solution for injection was obtained.

Formulation 3 solution for injection was placed under the conditions of 40° C. 2° C. for 5 days; compound II raw material (stored under refrigerated conditions of 2° C.-8° C.) was used as a control; and changes of related substances in the sample were examined, with data shown in Table 5.

TABLE 5

| Examination results of related substances of formulation 3 solution for injection | | |
|---|---|---|
| Sample | Sample storage condition | Total impurity (%) |
| Compound II | 0 days | 1.098 |
| Formulation 3 solution for injection | 40° C. ± 2° C., 5 days | 1.119 |

After formulation 3 solution for injection was placed at 40° C.±2° C. for high temperature acceleration for 5 days, the total impurity level was not significantly different from that of the raw material at day 0, indicating that formulation 3 solution for injection has a good stability.

Example 5 Formulation 4

| Substances | Content |
|---|---|
| Compound II | 0.10 g |
| Glacial acetic acid | 0.525 g |
| Sodium acetate | 0.207 g |
| Mannitol | 1.0 g |
| Water for injection, making up the volume to | 1000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Chengdu Kelong Chemical Co., Ltd.) and sodium acetate (source: Chengdu Jinshan Chemical Test Co., Ltd.) were added to the above-mentioned water for injection under stirring and then stirred to dissolution and clarification to obtain solution (1). Mannitol (source: Merck, Germany) was weighed, added to solution (1) and stirred to clarification to afford solution (2). Compound II was weighed, added to solution (2) and stirred to clarification, and a constant volume was achieved by adding water. The resulting solution was subjected to sterilizing filtration through a 0.22 μm filter and then subjected to filling and sealing, and formulation 4 solution for injection was obtained.

Formulation 4 solution for injection was placed under the conditions of 40° C. 2° C. for 9 days; compound II raw material (stored under refrigerated conditions of 2° C.-8° C.) was used as a control; and changes of related substances in the sample were examined, with data shown in Table 6.

TABLE 6

| Examination results of related substances of formulation 4 solution for injection | | |
|---|---|---|
| Sample | Sample storage condition | Total impurity (%) |
| Compound II | 0 days | 1.238 |
| Formulation 4 solution for injection | 40° C. ± 2° C., 9 days | 1.281 |

After formulation 4 solution for injection was placed at 40° C.±2° C. for high temperature acceleration for 9 days, the total impurity level was not significantly different from that of the raw material at day 0, indicating that formulation 4 solution for injection has a good stability.

Example 6 Formulation 5

The prescription was as follows:

| Substances | Content |
|---|---|
| Compound II | 0.10 g |
| Glacial acetic acid | 0.525 g |
| Anhydrous sodium acetate | 0.207 g |
| Mannitol | 10.0 g |
| Water for injection, making up the volume to | 1000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Chengdu Kelong Chemical Co., Ltd.) and sodium acetate (source: Chengdu Jinshan Chemical Test Co., Ltd.) were added to the above-mentioned water for injection under stirring and then stirred to dissolution and clarification to obtain solution (1). Mannitol (source: Merck, Germany) was weighed, added to solution (1) and stirred to clarification to afford solution (2). Compound II was weighed, added to solution (2) and stirred to clarification, and a constant volume was achieved by adding water. The resulting solution was subjected to sterilizing filtration through a 0.22 μm filter and then subjected to filling and sealing, and formulation 5 solution for injection was obtained.

Formulation 5 solution for injection was placed under the conditions of 40° C. 2° C. for 9 days; compound II raw material (stored under refrigerated conditions of 2° C.-8° C.) was used as a control; and changes of related substances in the sample were examined, with data shown in Table 7.

TABLE 7

Examination results of related substances of formulation 5 solution for injection

| Sample | Sample storage condition | Total impurity (%) |
|---|---|---|
| Compound II | 0 days | 1.238 |
| Formulation 5 solution for injection | 40° C. ± 2° C., 9 days | 1.279 |

After formulation 5 solution for injection was placed at 40° C.±2° C. for high temperature acceleration for 9 days, the total impurity level was not significantly different from that of the raw material at day 0, indicating that formulation 5 solution for injection has a good stability.

Example 7 Formulation 6

The prescription is as follows:

| Substances | Prescription |
|---|---|
| Compound II | 0.10 g |
| Glacial acetic acid | 0.466 g |
| Sodium acetate | 0.302 g |
| Mannitol | 50.0 g |
| Water for injection, making up the volume to | 1000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Chengdu Kelong Chemical Co., Ltd.) and sodium acetate (source: Chengdu Jinshan Chemical Test Co., Ltd.) were added to the above-mentioned water for injection under stirring and then stirred to dissolution and clarification to obtain solution (1). Compound II was weighed, added to solution (1) and stirred to clarification to afford solution (2). Mannitol (source: Qingdao Bright Moon Seaweed Group Co., Ltd.) was weighed, added to solution (2) and stirred to clarification, and a constant volume was achieved by adding water. The resulting solution was subjected to sterilizing filtration through a 0.22 μm filter and then subjected to filling and sealing, and formulation 6 solution for injection was obtained.

Formulation 6 solution for injection was placed under the conditions of 2° C.-8° C. and 25° C.±2° C., respectively, and changes of pH values and related substances of each sample were examined, with data shown in Table 8.

TABLE 8

Examination results of pH values and related substances of formulation 6 solution for injection

| Sample storage condition | pH value | Total impurity (%) |
|---|---|---|
| 2° C.-8° C., 81 days | 4.22 | 0.651 |
| 25° C. ± 2° C., 81 days | 4.22 | 0.686 |

Conclusion: Under storage conditions of different temperatures, the pH values and total impurity levels were substantially the same, and the content of the total impurity was low, indicating that formulation 6 has a good stability.

Example 8 Formulation 7

The prescription is as follows:

| Substances | Content |
|---|---|
| Compound II | 0.10 g |
| Glacial acetic acid | 0.466 g |
| Sodium acetate | 0.302 g |
| Glucose | 50.0 g |
| Water for injection, making up the volume to | 1000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Chengdu Kelong Chemical Co., Ltd.) and sodium acetate (source: Chengdu Jinshan Chemical Test Co., Ltd.) were added to the above-mentioned water for injection under stirring and then stirred to dissolution and clarification to obtain solution (1). Compound II was weighed, added to solution (1) and stirred to clarification to afford solution (2). Glucose (source: Weifang Shengtai Medicine Co., Ltd.) was weighed, added to solution (2) and stirred to clarification, and a constant volume was achieved by adding water. The resulting solution was subjected to sterilizing filtration through a 0.22 μm filter and then subjected to filling and sealing, and formulation 7 solution for injection was obtained.

Example 9 Formulation 8

The prescription is as follows:

| Substances | Content |
|---|---|
| Compound II | 0.2 g |
| Glacial acetic acid | 4.66 g |
| Anhydrous sodium acetate | 1.82 g |
| Water for injection, making up the volume to | 1000 ml |

Water for injection in a volume of 95% of the constant volume was measured and taken, and the water temperature was controlled to be 30° C. or less. Glacial acetic acid (source: Duksan Pure Chemicals Co., Ltd. of Republic of Korea) and sodium acetate trihydrate (source: Duksan Pure Chemicals Co., Ltd. of Republic of Korea) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and after passing the detection, formulation 8 solution for injection was obtained.

Example 10 Formulation 9

The prescription is as follows:

| Substances | Content |
|---|---|
| Compound II | 1.00 g |
| Glacial acetic acid | 4.66 g |
| Anhydrous sodium acetate | 1.82 g |
| Water for injection, making up the volume to | 1000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Taishan Xinning Pharmaceutical Co., Ltd.) and sodium acetate (source: Taishan Xinning Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and after passing the detection, formulation 9 solution for injection was obtained.

Example 11 Formulation 10

The prescription is as follows:

| Substances | Content |
|---|---|
| Compound II | 5.00 g |
| Glacial acetic acid | 4.66 g |
| Anhydrous sodium acetate | 1.82 g |
| Water for injection, making up the volume to | 1000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Taishan Xinning Pharmaceutical Co., Ltd.) and sodium acetate (source: Taishan Xinning Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 10 solution for injection was obtained.

Formulation 8 solution for injection obtained in Example 9 was placed under the conditions of 25° C.±2° C. and RH 60%±5%, and 2° C.-8° C.; the quality indicators of the preparation were measured 3 months later; and the results are shown in Table 9.

TABLE 9

Stability of formulation 8 solution for injection

| Condition | 2° C.-8° C. | 25° C. |
|---|---|---|
| Time | 3 months | 3 months |
| Character | Colorless clear liquid | Colorless clear liquid |
| pH value | 4.23 | 4.28 |
| Total impurity (%) | 0.291 | 0.317 |

Conclusion: Compared with the sample under the conditions of 2° C.-8° C. for 3 months, the sample under the conditions of 25° C. for 3 months showed no significant difference in various quality indicators, indicating that the stability of formulation 8 solution for injection was good within 3 months.

Formulation 9 solution for injection obtained in Example 10 was placed under the conditions of 25° C.±2° C. and RH 60%±50%; the quality indicators of the preparation were measured 6 months later; and the results are shown in Table 10.

TABLE 10

Stability of formulation 9 solution for injection

| | | 0 months | 6 months |
|---|---|---|---|
| Time | | 0 months | 6 months |
| Character | | Colorless clear liquid | Colorless clear liquid |
| pH value | | 4.3 | 4.3 |
| Color | | Colorless | Colorless |
| Related substances | Maximum individual impurity (%) | 0.28 | 0.29 |
| | Total impurity (%) | 0.90 | 1.05 |
| Content (%) | | 102.2 | 102.5 |

Conclusion: Compared with the sample at month 0, the sample at month 6 showed no significant change in various quality indicators, indicating that formulation 9 solution for injection has a good stability.

Formulation 10 solution for injection prepared in Example 11 was placed under the conditions of 25° C.±2° C. and RH 60%±500; the quality indicators of the preparation were measured 6 months later; and the results are shown in Table 11.

TABLE 11

Stability of formulation 10 solution for injection

| | | |
|---|---|---|
| Time | 0 months | 6 months |
| Character | Colorless clear liquid | Colorless clear liquid |

TABLE 11-continued

| Stability of formulation 10 solution for injection | | | |
|---|---|---|---|
| | pH value | 4.5 | 4.5 |
| | Color | Colorless | Colorless |
| Related substances | Maximum individual impurity (%) | 0.20 | 0.21 |
| | Total impurity (%) | 0.91 | 0.99 |
| | Content (%) | 99.9 | 100.2 |

Conclusion: Compared with the sample at month 0, the sample at month 6 showed no significant change in various quality indicators, indicating that the sample obtained in the present disclosure has a good stability.

Example 12 Formulation 11

The prescription is as follows:

| Substances | Content |
|---|---|
| Compound II | 0.10 g |
| Glacial acetic acid | 4.66 g |
| Anhydrous sodium acetate | 1.82 g |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Taishan Xinning Pharmaceutical Co., Ltd.) and sodium acetate (source: Taishan Xinning Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 11 solution for injection was obtained.

Example 13 Formulation 12

The prescription is as follows:

| Substances | Content |
|---|---|
| Compound II | 10.00 g |
| Glacial acetic acid | 13.98 g |
| Anhydrous sodium acetate | 5.46 g |
| Water for injection, making up the volume to | 10000 ml |

Water for injection in a volume of 90% of the constant volume was measured and taken; nitrogen was charged beneath the surface of the liquid for 20 min or longer; and the water temperature was controlled to be 30° C. or less. Glacial acetic acid (source: Taishan Xinning Pharmaceutical Co., Ltd.) and sodium acetate (source: Taishan Xinning Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 12 solution for injection was obtained.

Example 14 Formulation 13

The prescription is as follows:

| Substances | Content |
|---|---|
| Compound II | 50.00 g |
| Glacial acetic acid | 46.6 g |
| Anhydrous sodium acetate | 18.2 g |
| Water for injection, making up the volume to | 10000 ml |

Water for injection in a volume of 90% of the constant volume was measured and taken; nitrogen was charged beneath the surface of the liquid for 20 min or longer; and the water temperature was controlled to be 30° C. or less. Glacial acetic acid (source: Taishan Xinning Pharmaceutical Co., Ltd.) and sodium acetate (source: Taishan Xinning Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 13 solution for injection was obtained.

Example 15 Formulation 14

The prescription is as follows:

| Substances | Content |
|---|---|
| Compound II | 1.00 g |
| Mannitol | 500 g |
| Edetate disodium | 0.5 g |
| Glacial acetic acid | 4.66 g |
| Anhydrous sodium acetate | 1.82 g |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Mannitol (source: Qingdao Bright Moon Seaweed Group Co., LTD.), glacial acetic acid (source: Taishan Xinning Pharmaceutical Co., Ltd.), sodium acetate (source: Taishan Xinning Pharmaceutical Co., Ltd.) and edetate disodium (source: Hunan Er-kang Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 14 solution for injection was obtained.

Example 16 Formulation 15

The prescription is as follows:

| Substances | Content |
|---|---|
| Compound II | 10.00 g |
| Mannitol | 500 g |
| Edetate disodium | 0.5 g |
| Glacial acetic acid | 23.3 g |
| Anhydrous sodium acetate | 9.1 g |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Mannitol (source: Qingdao Bright Moon Seaweed Group Co., LTD.), glacial acetic acid (source: Taishan Xinning Pharmaceutical Co., Ltd.), sodium acetate (source: Taishan Xinning Pharmaceutical Co., Ltd.) and edetate disodium (source: Hunan Er-kang Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 15 solution for injection was obtained.

Example 17 Formulation 16

The prescription is as follows:

| Substances | Content |
|---|---|
| Compound II | 0.10 g |
| Mannitol | 500 g |
| Edetate disodium | 0.5 g |
| Glacial acetic acid | 4.66 g |
| Anhydrous sodium acetate | 1.82 g |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Mannitol (source: Qingdao Bright Moon Seaweed Group Co., LTD.), glacial acetic acid (source: Taishan Xinning Pharmaceutical Co., Ltd.), sodium acetate (source: Taishan Xinning Pharmaceutical Co., Ltd.) and edetate disodium (source: Hunan Er-kang Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 16 solution for injection was obtained.

Example 18 Formulation 17

The prescription is as follows:

| Substances | Content |
|---|---|
| Compound II | 2.00 g |
| Mannitol | 100 g |
| Edetate disodium | 0.5 g |
| Glacial acetic acid | 9.32 g |
| Anhydrous sodium acetate | 3.64 g |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Mannitol (source: Qingdao Bright Moon Seaweed Group Co., LTD.), glacial acetic acid (source: Taishan Xinning Pharmaceutical Co., Ltd.), sodium acetate (source: Taishan Xinning Pharmaceutical Co., Ltd.) and edetate disodium (source: Hunan Er-kang Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 17 solution for injection was obtained.

Example 19 Formulation 18

The prescription is as follows:

| Substances | Content |
|---|---|
| Compound II | 1.00 g |
| Edetate disodium | 0.5 g |
| Glacial acetic acid | 4.66 g |
| Anhydrous sodium acetate | 1.82 g |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Glacial acetic acid (source: Taishan Xinning Pharmaceutical Co., Ltd.), sodium acetate (source: Taishan Xinning Pharmaceutical Co., Ltd.) and edetate disodium (source: Hunan Er-kang Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 18 solution for injection was obtained.

Example 20 Formulation 19

The prescription is as follows:

| Substances | Content |
|---|---|
| Compound II | 1.00 g |
| Edetate disodium | 1.00 g |
| Glacial acetic acid | 4.66 g |
| Anhydrous sodium acetate | 1.82 g |
| Water for injection, making up the volume to | 10000 ml |

Water for injection in a volume of 95% of the constant volume was measured and taken, and the water temperature was controlled to be 30° C. or less. Glacial acetic acid (source: Taishan Xinning Pharmaceutical Co., Ltd.), sodium acetate (source: Taishan Xinning Pharmaceutical Co., Ltd.) and edetate disodium (source: Hunan Er-kang Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 19 solution for injection was obtained.

Example 21 Formulation 20

The prescription is as follows:

| Substances | Content |
|---|---|
| Compound II | 1.00 g |
| Trehalose | 200 g |
| Glacial acetic acid | 4.66 g |
| Anhydrous sodium acetate | 1.82 g |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Trehalose (source: Ron Pharm), glacial acetic acid (source: Taishan Xinning Pharmaceutical Co., Ltd.) and sodium acetate (source: Taishan Xinning Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 20 solution for injection was obtained.

Example 22 Formulation 21

The prescription is as follows:

| Substances | Content |
|---|---|
| Compound II | 5.00 g |
| Sodium chloride | 90.00 g |
| Sodium phosphate | 31.20 g |
| Phosphoric acid | Adjusting the pH value to 3-5.5 |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Sodium chloride (source: Tianjin Haiguang Pharmaceutical Co., Ltd.) and sodium phosphate (source: Sichuan Xilong Chemical Co., Ltd.) were weighed, added to the above-mentioned water for injection under stirring, and then stirred to dissolution and clarification and adjusted with phosphoric acid (source: Chengdu Kelong Chemical Co., Ltd.) to a pH value of 3-5.5 to obtain solution (1). Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 21 solution for injection was obtained.

Example 23 Formulation 22

The prescription is as follows:

| Substances | Content |
|---|---|
| Compound II | 5.00 g |
| Sodium chloride | 90.00 g |
| Sodium benzoate | 10.00 g |
| Tartaric acid | Adjusting the pH to 3-5.5 |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Sodium benzoate (source: Chengdu Huayi Pharmaceutical Excipient Manufacturing Co., Ltd.) and sodium chloride (source: Tianjin Haiguang Pharmaceutical Co., Ltd.) were weighed, added to the above-mentioned water for injection under stirring, and then stirred to dissolution and clarification to obtain solution (1). Compound II was weighed, added to solution (1) and stirred until complete dissolution. An appropriate amount of tartaric acid was added to adjust the pH to 3-5.5, and a constant volume was achieved by adding water. The resulting solution was subjected to sterilizing filtration through a 0.22 μm filter and then subjected to filling and sealing; a leak detection was carried out; and formulation 22 solution for injection was obtained.

Example 24 Formulation 23

The prescription is as follows:

| Substances | Content |
|---|---|
| Compound II | 1.00 g |
| Tartaric acid | 15 g |

-continued

| Substances | Content |
|---|---|
| Sodium hydroxide | Adjusting the pH to 3-5.5 |
| Trehalose | 1000 g |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Trehalose (source: Ron Pharm) and tartaric acid (source: Chengdu Kelong Chemical Reagent Factory) were weighed, added to the above-mentioned water for injection under stirring, and then stirred to dissolution and clarification; an appropriate amount of sodium hydroxide (Sichuan Xilong Chemical Co., Ltd.) was added to adjust the pH to 3-5.5; and solution (1) was obtained. Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 23 solution for injection was obtained.

Formulation 23 solution for injection obtained in Example 24 was placed under the conditions of 25° C.±2° C. and RH 60%±5%; the quality indicators of the preparation were measured 1 month later; and the results are shown in Table 12.

TABLE 12

Stability of formulation 23 solution for injection

| | 0 months | 25° C. 1 month |
|---|---|---|
| Character | Colorless clear liquid | Colorless clear liquid |
| pH value | 4.22 | 4.53 |
| Total impurity (%) | 0.565 | 0.608 |

Conclusion: Compared with the sample at month 0, the sample at month 1 showed no significant change in various quality indicators, indicating that formulation 23 solution for injection has a good stability.

Example 25 Formulation 24

The prescription is as follows:

| Substances | Content |
|---|---|
| Compound II | 1.00 g |
| Tartaric acid | 15 g |
| Sodium hydroxide | Adjusting the pH to 3-5.5 |
| Trehalose | 400 g |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Trehalose (source: Ron Pharm) and tartaric acid (source: Chengdu Kelong Chemical Reagent Factory) were weighed, added to the above-mentioned water for injection under stirring, and then stirred to dissolution and clarification; an appropriate amount of sodium hydroxide (Sichuan Xilong Chemical Co., Ltd.) was added to adjust the pH to 3-5.5; and solution (1) was obtained. Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 24 solution for injection was obtained.

Formulation 24 solution for injection obtained in Example 25 was placed under the conditions of 40° C.±2° C. and RH 75%±5%; the quality indicators of the preparation were measured 15 d later; and the results are shown in Table 13.

TABLE 13

Stability of formulation 24 solution for injection

| Time | 0 months | 40° C. 15 d |
|---|---|---|
| Character | Colorless clear liquid | Colorless clear liquid |
| pH value | 4.20 | 4.20 |
| Total impurity (%) | 0.560 | 0.628 |

Conclusion: Compared with the sample at month 0, the sample under the conditions of 40° C. for 15 d showed no significant change in various quality indicators, indicating that formulation 24 solution for injection has a good stability.

Example 26 Formulation 25

| Substances | Content |
|---|---|
| Compound II | 1.00 g |
| Tartaric acid | 15 g |
| Sodium hydroxide | Adjusting the pH to 3-5.5 |
| Water for injection, making up the volume to | 10000 ml |

Water for injection in a volume of 95% of the constant volume was measured and taken; nitrogen was charged beneath the surface of the liquid for 20 min or longer; and the water temperature was controlled to be 30° C. or less. Tartaric acid (source: Chengdu Kelong Chemical Reagent Factory) was weighed, added to the above-mentioned water for injection under stirring, and then stirred to dissolution and clarification; an appropriate amount of sodium hydroxide (source: Chengdu Kelong Chemical Co., Ltd.) was added to adjust the pH to 3-5.5; and solution (1) was obtained. Compound II was weighed, added to solution (1) and stirred until complete dissolution, and a constant volume was achieved by adding water. The resulting solution was subjected to sterilizing filtration through a 0.22 μm filter and then subjected to filling and sealing; a leak detection was carried out; and formulation 25 solution for injection was obtained.

Formulation 25 solution for injection obtained in Example 26 was placed under the conditions of 25° C.±2° C. and RH 60%±5%; the quality indicators of the preparation were measured 13 d later; and the results are shown in Table 14.

TABLE 14

| Stability of formulation 25 solution for injection | | |
|---|---|---|
| | 0 months | 25° C. 13 d |
| Character | Colorless clear liquid | Colorless clear liquid |
| pH value | 4.18 | 4.20 |
| Total impurity (%) | 0.518 | 0.487 |

Conclusion: Compared with the sample at month 0, the sample under the conditions of 25° C. for 13 d showed no significant change in various quality indicators, indicating that formulation 25 solution for injection has a good stability.

Sterile lyophilized powder for injection:

Example 27 Formulation 26

| Substances | Content |
|---|---|
| Compound II | 1.00 g |
| Trehalose | 400 g |
| Tartaric acid | 15 g |
| Sodium hydroxide | Adjusting the pH to 3-5.5 |
| Water for injection, making up the volume to | 10000 ml |

Water for injection in a volume of 95% of the constant volume was measured and taken, and the water temperature was controlled to be 30° C. or less. Trehalose (source: Ron Pharm) and tartaric acid (source: Chengdu Kelong Chemical Reagent Factory) were weighed and added to the above-mentioned water for injection under stirring; sodium hydroxide (source: Chengdu Kelong Chemical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

Formulation 26 lyophilized sample prepared in Example 27 was placed under the conditions of 25° C.±2° C. and RH 60%±5%; the quality indicators of the preparation were measured 6 months later; and the results are shown in Table 15.

TABLE 15

| Stability of formulation 26 lyophilized sample | | | | |
|---|---|---|---|---|
| | 0 months | 10 days | 3 months | 6 months |
| Character | White loose solid | White loose solid | White loose solid | White loose solid |
| Appearance of reconstituted solution | Colorless clear solution | Colorless clear solution | Colorless clear solution | Colorless clear solution |
| pH of reconstituted solution | 4.15 | 4.17 | \ | 4.20 |
| Total impurity | 0.614 | 0.577 | 0.621 | 0.629 |

Conclusion: Compared with the sample at month 0, the sample within 6 months showed no significant change in various quality indicators, indicating that the sample obtained in the present disclosure has a good stability.

Example 28 Formulation 27

| Substances | Content |
|---|---|
| Compound II | 0.2 g |
| Trehalose | 400 g |
| Tartaric acid | 15 g |
| Sodium hydroxide | Adjusting the pH to 3-5.5 |
| Water for injection, making up the volume to | 10000 ml |

Water for injection in a volume of 95% of the constant volume was measured and taken, and the water temperature was controlled to be 30° C. or less. Trehalose (source: Ron Pharm) and tartaric acid (source: Hunan Er-kang Pharmaceutical Co., Ltd.) were weighed and added to the above-mentioned water for injection under stirring; sodium hydroxide (source: Hunan Er-kang Pharmaceutical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

Example 29 Formulation 28

| Substances | Content |
|---|---|
| Compound II | 5 g |
| Trehalose | 400 g |
| Tartaric acid | 15 g |
| Sodium hydroxide | Adjusting the pH to 3-5.5 |
| Water for injection, making up the volume to | 10000 ml |

Water for injection in a volume of 95% of the constant volume was measured and taken, and the water temperature was controlled to be 30° C. or less. Trehalose (source: Ron Pharm) and tartaric acid (source: Hunan Er-kang Pharmaceutical Co., Ltd.) were weighed and added to the above-mentioned water for injection under stirring; sodium hydroxide (source: Hunan Er-kang Pharmaceutical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

Example 30 Formulation 29

| Substances | Content |
|---|---|
| Compound II | 1.00 g |
| Trehalose | 1000 g |
| Tartaric acid | 15 g |
| Sodium hydroxide | Adjusting the pH to 3-5.5 |
| Water for injection, making up the volume to | 10000 ml |

Water for injection in a volume of 95% of the constant volume was measured and taken, and the water temperature was controlled to be 30° C. or less. Trehalose (source: Ron Pharm) and tartaric acid (source: Hunan Er-kang Pharmaceutical Co., Ltd.) were weighed and added to the above-mentioned water for injection under stirring; sodium hydroxide (source: Hunan Er-kang Pharmaceutical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

Example 31 Formulation 30

| Substances | Content |
|---|---|
| Compound II | 1.00 g |
| Lactose | 400 g |
| Tartaric acid | 15 g |
| Sodium hydroxide | Adjusting the pH to 3-5.5 |
| Water for injection, making up the volume to | 10000 ml |

Water for injection in a volume of 95% of the constant volume was measured and taken, and the water temperature was controlled to be 30° C. or less. Lactose (source: MEGGLE GmbH & Co. KG, Germany) and tartaric acid (source: Hunan Er-kang Pharmaceutical Co., Ltd.) were weighed and added to the above-mentioned water for injection under stirring; sodium hydroxide (source: Hunan Er-kang Pharmaceutical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

Example 32 Formulation 31

| Substances | Content |
|---|---|
| Compound II | 1.00 g |
| Sucrose | 400 g |
| Tartaric acid | 15 g |
| Sodium hydroxide | Adjusting the pH to 3-5.5 |
| Water for injection, making up the volume to | 10000 ml |

Water for injection in a volume of 95% of the constant volume was measured and taken, and the water temperature was controlled to be 30° C. or less. Sucrose (source: Merck, Germany) and tartaric acid (source: Hunan Er-kang Pharmaceutical Co., Ltd.) were weighed and added to the above-mentioned water for injection under stirring; sodium hydroxide (source: Hunan Er-kang Pharmaceutical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

Example 33 Formulation 32

| Substances | Content |
|---|---|
| Compound II | 1.00 g |
| Hydroxypropyl-β-cyclodextrin | 400 g |
| Tartaric acid | 15 g |
| Sodium hydroxide | Adjusting the pH to 3-5.5 |
| Water for injection, making up the volume to | 10000 ml |

Water for injection in a volume of 95% of the constant volume was measured and taken, and the water temperature was controlled to be 30° C. or less. Hydroxypropyl-β-cyclodextrin (source: Roquette, France) and tartaric acid (source: Hunan Er-kang Pharmaceutical Co., Ltd.) were weighed and added to the above-mentioned water for injection under stirring; sodium hydroxide (source: Hunan Er-kang Pharmaceutical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

Example 34 Formulation 33

| Substances | Content |
|---|---|
| Compound II | 1.00 g |
| Trehalose | 400 g |
| Tartaric acid | 45 g |
| Sodium hydroxide | Adjusting the pH to 3-5.5 |
| Water for injection, making up the volume to | 10000 ml |

Water for injection in a volume of 95% of the constant volume was measured and taken, and the water temperature was controlled to be 30° C. or less. Trehalose (source: Ron Pharm) and tartaric acid (source: Hunan Er-kang Pharmaceutical Co., Ltd.) were weighed and added to the above-mentioned water for injection under stirring; sodium hydroxide (source: Hunan Er-kang Pharmaceutical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

Example 35 Formulation 34

| Substances | Content |
|---|---|
| Compound II | 1.00 g |
| Trehalose | 400 g |
| Tartaric acid | 7.5 g |
| Sodium hydroxide | Adjusting the pH to 3-5.5 |
| Water for injection, making up the volume to | 10000 ml |

Water for injection in a volume of 95% of the constant volume was measured and taken, and the water temperature was controlled to be 30° C. or less. Trehalose (source: Ron Pharm) and tartaric acid (source: Hunan Er-kang Pharmaceutical Co., Ltd.) were weighed and added to the above-mentioned water for injection under stirring; sodium hydroxide (source: Hunan Er-kang Pharmaceutical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

Example 36 Formulation 35

| Substances | Content |
|---|---|
| Compound II | 10.00 g |
| Trehalose | 500 g |

-continued

| Substances | Content |
|---|---|
| Sodium phosphate | 78.01 g |
| Phosphoric acid | Adjusting the pH to 3-5.5 |
| Water for injection, making up the volume to | 10000 ml |

Water for injection in a volume of 95% of the constant volume was measured and taken, and the water temperature was controlled to be 30° C. or less. Trehalose (source: Ron Pharm) and sodium phosphate (source: Sichuan Xilong Chemical Co., Ltd.) were weighed and added to the above-mentioned water for injection under stirring; phosphoric acid (source: Chengdu Kelong Chemical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

Example 37 Formulation 36

| Substances | Content |
|---|---|
| Compound II | 0.1 g |
| Trehalose | 400 g |
| Tartaric acid | 15 g |
| Sodium hydroxide | Adjusting the pH to 3-5.5 |
| Water for injection, making up the volume to | 10000 ml |

Water for injection in a volume of 95% of the constant volume was measured and taken, and the water temperature was controlled to be 30° C. or less. Trehalose (source: Ron Pharm) and tartaric acid (source: Hunan Er-kang Pharmaceutical Co., Ltd.) were weighed and added to the above-mentioned water for injection under stirring; sodium hydroxide (source: Hunan Er-kang Pharmaceutical Co., Ltd.) was used to adjust the pH value to 3-5.5; and the mixture was stirred to dissolution and clarification to obtain solution (1).

Compound II was weighed, added to solution (1) and stirred until complete dissolution, and a constant volume was achieved by adding water.

Following sterilizing filtration through a 0.22 μm filter, filling and sealing were carried out, wherein the resulting solution was filled into 3 ml penicillin vials in a loading amount of 1 ml/vial, and the vials were partially stoppered and placed in a lyophilizer for pre-freezing.

Partition boards were cooled to −35° C. or lower which was maintained for 1-2 h; then a chamber was cooled to −50° C. or lower and vacuumed to 20 Pa or lower; a limited leakage valve was opened and the temperature was raised to −5° C. over 5 h which was maintained for another 2 h; the temperature was raised to 10° C. over 4 h which was maintained until the temperature of the preparation reached 0° C. or higher; the temperature was risen to 35° C. over 3 h which was maintained until the temperature of the preparation reached 25° C. or higher; and then the limited leakage valve was closed, and the temperature was maintained for 2 h.

Vacuuming or charging nitrogen was performed, and the vials were completely stoppered, taken out from the chamber and capped.

The above embodiments are only preferred embodiments of the present disclosure and are not intended to limit the present disclosure. For those skilled in the art, several improvements, modifications, and equivalent replacements may also be made without departing from the principle of the present disclosure, and these improvements, modifications, and equivalent replacements shall be contained within the scope of protection of the present disclosure.

The invention claimed is:

1. A pharmaceutical composition consisting of a compound of formula (I) or a pharmaceutically acceptable salt thereof and a pH regulator, wherein the composition has a pH value of 3-5.5, and the pH regulator is a buffer consisting of acids and corresponding salts thereof and has a pH value of 3-5.5, (I)

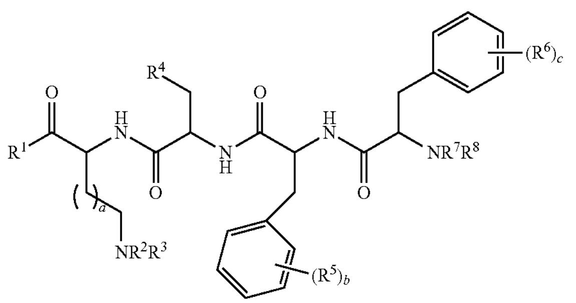

wherein $R^1$ is selected from

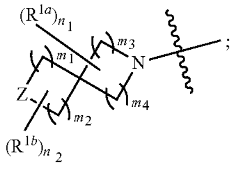

$m_1$ and $m_2$ are each independently selected from 1, 2, 3 or 4;

$m_3$ and $m_4$ are each independently selected from 0, 1, 2, 3 or 4, provided that $m_3$ and $m_4$ are not both 0;

$n_1$ and $n_2$ are each independently selected from 0, 1, 2, 3 or 4;

Z is selected from $CR^{z1}R^{z2}$ or $NR^{z3}$;

$R^{z1}$ and $R^{z2}$ are each independently selected from H, F, Cl, Br, I, OH, $CF_3$, nitro, $C_{1-6}$alkyl, $C_{1-6}$alkoxy, $C_{2-6}$alkenyl, $C_{2-6}$alkynyl, —C(═O)—$C_{1-6}$alkyl, —$(CH_2)_q$—C(═O)O—$C_{1-6}$alkyl, —$(CH_2)_q$—$NR^{1e}R^{1f}$, —$(CH_2)_q$—COOH, —$(CH_2)_q$—$CONH_2$, $C_{3-8}$carbocyclyl, or 3- to 8-membered heterocyclyl, wherein the alkyl, alkoxy, alkenyl, alkynyl, carbocyclyl or heterocyclyl is optionally further substituted with 0-5 substituents selected from F, Cl, Br, I, OH, $CF_3$, ═O, carboxyl, nitro, cyano, amino, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, the heterocyclyl contains 1 to 3 heteroatoms optionally selected from N, O or S, and when the heteroatom is S, the heterocyclyl can optionally contain S, S═O or S(═O)$_2$;

$R^{1e}$ and $R^{1f}$ are each independently selected from H, $C_{1-6}$alkyl, —C(═O)O—$C_{1-6}$alkyl, —C(═O)O—$(CH_2)_q$—$C_{3-8}$carbocyclyl, or —C(═O)O—$(CH_2)_q$-3- to 8-membered heterocyclyl, wherein the alkyl, carbocyclyl or heterocyclyl is optionally further substituted with 0-5 substituents selected from F, Cl, Br, I, OH, $CF_3$, cyano, nitro, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, and the heterocyclyl contains 1 to 3 heteroatoms selected from N, O or S;

or $R^{z1}$ and $R^{z2}$ together with the carbon atoms to which they are attached form a 3- to 10-membered nitrogen-containing heterocyclic ring, wherein the ring is optionally further substituted with a substituent selected from F, Cl, Br, I, OH, $CF_3$, cyano, nitro, ═O, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl;

$R^{1a}$ and $R^{1b}$ are each independently selected from F, $CF_3$, $C_{1-6}$alkyl, $C_{2-6}$alkenyl, $C_{2-6}$alkynyl or 3- to 8-membered heterocyclyl, wherein the alkyl, alkenyl, alkynyl or heterocyclyl is optionally further substituted with 0-5 substituents selected from F, Cl, Br, I, OH, $CF_3$, nitro, cyano, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, and the heterocyclyl contains 1 to 3 heteroatoms optionally selected from N, O or S;

$R^{z3}$ is independently selected from H, —C(═O)—$C_{1-6}$ alkyl, —C(═O)O—$C_{1-6}$alkyl, —C(═O)—$C_{3-8}$carbocyclyl, —C(═O)O—$C_{3-8}$carbocyclyl, —C(═O)O-(3- to 8-membered heterocyclyl), —S(═O)$_p$—$C_{1-6}$ alkyl, —S(═O)$_p$—$C_{3-8}$carbocyclyl, —S(═O)$_p$-(3- to 8-membered heterocyclyl), —C(═O)$NR^{1g}R^{1h}$, —S(═O)$_p$—$NR^{1i}R^{1j}$ or 3- to 8-membered heterocyclyl, wherein the alkyl, carbocyclyl or heterocyclyl is optionally further substituted with 0-5 substituents selected from F, Cl, Br, I, OH, $CF_3$, nitro, cyano, amino, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, and the heterocyclyl contains 1 to 3 heteroatoms optionally selected from N, O or S;

$R^{1g}$, $R^{1h}$, $R^{1i}$, and $R^{1j}$ are each independently selected from H or $C_{1-6}$alkyl;

or $R^{1g}$ and $R^{1h}$ together with the nitrogen atoms to which they are attached form a 3- to 10-membered heterocyclic ring, wherein the ring is optionally further substituted with a substituent selected from F, Cl, Br, I, OH, $CF_3$, cyano, nitro, $C_{1-6}$alkyl, $C_{1-6}$alkoxy, $C_{2-6}$alkenyl, $C_{2-6}$alkynyl or $—S(═O)_p—C_{1-6}$alkyl, and the heterocyclic ring contains 1 to 3 heteroatoms selected from N, O or S;

q is selected from 0, 1, 2, 3 or 4;

p is selected from 0, 1 or 2;

a is selected from 0, 1, 2 or 3;

$R^4$ is independently selected from H, $C_{1-6}$alkyl, $C_{2-6}$alkenyl, $C_{2-6}$alkynyl or $—(CH_2)_q—C_{3-8}$carbocyclyl, wherein the alkyl, alkenyl, alkynyl or carbocyclyl is optionally further substituted with 0-5 substituents selected from F, Cl, Br, I, OH, CN, $CF_3$, $NO_2$, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, and the heterocyclyl contains 1 to 3 heteroatoms selected from N, O or S;

$R^2$, $R^3$, $R^7$ and $R^8$ are each independently selected from H, $C_{1-6}$alkyl, $—C(═O)O—C_{1-4}$alkyl, $—C(═O)O—(CH_2)_q—C_{3-8}$carbocyclyl, $—C(═O)O—(CH_2)_q$-3- to 8-membered heterocyclyl or

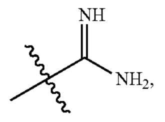 [SMILES: *C(=N)N]

wherein the alkyl, carbocyclyl or heterocyclyl is optionally further substituted with 0-5 substituents selected from F, Cl, Br, I, OH, $CF_3$, nitro, cyano, $C_{1-6}$alkyl, $C_{1-6}$alkoxy, $C_{2-6}$alkenyl, $C_{2-6}$alkynyl, $C_{3-8}$carbocyclyl or 3- to 8-membered heterocyclyl, and the heterocyclyl contains 1 to 3 heteroatoms optionally selected from N, O or S;

b is selected from 0, 1, 2, 3, 4 or 5;

c is selected from 0, 1, 2, 3, 4 or 5;

$R^5$ and $R^6$ are each independently selected from F, Cl, Br, I, $CF_3$, cyano, nitro, $C_{1-4}$alkyl, $—OR^{5a}$, $—C(O)OR^{5b}$, $—SR^{5c}$, $—S(O)R^{5d}$, $+S(O)_2R^{5e}$ or $—NR^{5f}R^{5g}$;

$R^{5a}$, $R^{5b}$, $R^{5c}$, $R^{5d}$, $R^{5e}$, $R^{5f}$ and $R^{5g}$ are each independently selected from H or $C_{1-4}$alkyl;

or $R^{5f}$ and $R^{5g}$ together with the nitrogen atoms to which they are attached form a 5- to 6-membered heterocyclic ring, wherein the heterocyclic ring contains 1 to 3 heteroatoms optionally selected from N, O or S.

2. The composition according to claim 1, wherein the compound of formula (I) has a structure of formula (II):

(II)

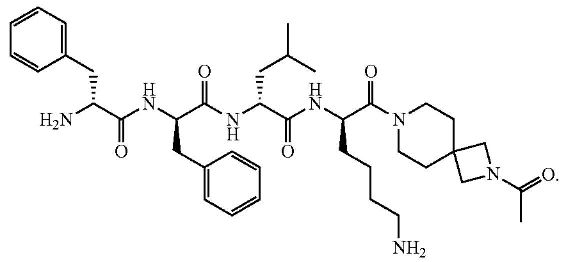

3. The composition according to claim 1, wherein the acid is selected from acetic acid, phosphoric acid, tartaric acid, or benzoic acid.

4. The composition according to claim 1, wherein the acid and corresponding salt is selected from an acetic acid-sodium acetate buffer, a tartaric acid-sodium hydrogen tartarate buffer, or a tartaric acid-sodium hydrogen tartarate-sodium tartrate concomitant buffer.

5. The composition according to claim 4, wherein the pH regulator is at a concentration of 1 mmol/L-500 mmol/L.

6. The composition according to claim 3, wherein the tartaric acid is selected from D-tartaric acid, L-tartaric acid or a racemate thereof.

7. The composition according to claim 1, wherein the compound of formula (I) has a weight/volume, w/v, of 0.001%-1%.

8. The composition according to claim 1, wherein the composition is a solution for injection or a sterile lyophilized powder for injection obtained by lyophilizing the solution.

9. A method for preparing the composition according to claim 1, the method comprising the following steps:

(1) dissolving ingredients, other than an active substance, in water for injection;

(2) adding the active substance to the solution obtained in step (1), wherein the active substance is the compound of formula (I) or a pharmaceutically acceptable salt thereof, to obtain a solution preparation; and (3) adding water to a constant volume to the solution preparation, carrying out sterilizing filtration of the solution preparation through a 0.22 μm filter, and filling and sealing the solution preparation in a pyrogen-free vial.

10. A method for preparing the composition according to claim 1, the method comprising the following steps the following steps:

(1) dissolving the pH regulator to water for injection;

(2) adding the active substance to the solution obtained in step (1) to obtain a solution preparation, wherein the active substance is the compound of formula (I) or a pharmaceutically acceptable salt thereof;

(3) adjusting the pH value with the pH regulator to a range of 3.0-5.5; and (4) adding water to a constant volume to the solution preparation, carrying out sterilizing filtration of the solution preparation through a 0.22 μm filter, and filling and sealing the solution preparation in a pyrogen-free vial.

11. The method according to claim 10, further comprising a lyophilizing step.

12. The method according to claim 11, wherein the lyophilizing step comprises:

(1) pre-freezing;

(2) cooling partition boards to −35° C. or lower and maintaining for 1-2 h; then cooling a chamber to −50° C. or lower and vacuuming to 20 Pa or lower; opening a limited leakage valve; raising the temperature to −5° C. over 3-5 h and maintaining for another 1-3 h; raising the temperature to 10° C. over 2-4 h and maintaining until the temperature of the preparation reaches 0° C. or higher; raising the temperature to 35° C. over 2-3 h and maintaining until the temperature of the preparation reaches 25° C. or higher; and then closing the limited leakage valve and maintaining the temperature for 1-3 h; and (3) vacuuming or charging nitrogen, completely stoppering, and then taking out from the chamber and capping.

13. A method for treating or preventing a disease or condition associated with kappa opioid receptors in a mammal, wherein the method comprises administering the composition according to claim 1.

14. The method according to claim 13, wherein the disease or condition associated with kappa opioid receptors is selected from the group consisting of pain, inflammation, itching, edema, hyponatremia, hypokalemia, intestinal obstruction, cough and glaucoma.

15. The method according to claim 14, wherein the pain is selected from neuropathic pain, somatic pain, visceral pain and skin pain.

16. The composition according to claim 4, wherein the pH regulator is at a concentration of 10 mmol/L-50 mmol/L.

17. The composition according to claim 1, wherein the compound of formula (I) has a weight/volume, w/v, of 0.002%-0.05%.

18. The method according to claim 9, further comprising a lyophilizing step.

19. The method according to claim 18, wherein the lyophilizing step comprises:

(1) pre-freezing;

(2) cooling partition boards to −35° C. or lower and maintaining for 1-2 h; then cooling a chamber to −50° C. or lower and vacuuming to 20 Pa or lower; opening a limited leakage valve; raising the temperature to −5° C. over 3-5 h and maintaining for another 1-3 h; raising the temperature to 10° C. over 2-4 h and maintaining until the temperature of the preparation reaches 0° C. or higher; raising the temperature to 35° C. over 2-3 h and maintaining until the temperature of the preparation reaches 25° C. or higher; and then closing the limited leakage valve and maintaining the temperature for 1-3 h; and (3) vacuuming or charging nitrogen, completely stoppering, and then taking out from the chamber and capping.

* * * * *